(12) United States Patent
Hirakoso et al.

(10) Patent No.: US 7,045,645 B2
(45) Date of Patent: May 16, 2006

(54) RUTHENIUM COMPOUNDS, PROCESS FOR THEIR PREPARATION, AND RUTHENIUM-CONTAINING THIN FILMS MADE BY USING THE COMPOUNDS

(75) Inventors: Hideyuki Hirakoso, Yokohama (JP); Masayuki Ishikawa, Sanda (JP); Akio Yanagisawa, Naka-gun (JP); Katsumi Ogi, Minami-saitama-gun (JP)

(73) Assignee: Mitsubishi Materials Corporation, Tokyo (JP)

( * ) Notice: Subject to any disclaimer, the term of this patent is extended or adjusted under 35 U.S.C. 154(b) by 0 days.

(21) Appl. No.: 10/499,822

(22) PCT Filed: Jan. 8, 2003

(86) PCT No.: PCT/JP03/00074

§ 371 (c)(1),
(2), (4) Date: Jul. 6, 2004

(87) PCT Pub. No.: WO03/057706

PCT Pub. Date: Jul. 17, 2003

(65) Prior Publication Data

US 2005/0090679 A1 Apr. 28, 2005

(30) Foreign Application Priority Data

Jan. 8, 2002 (JP) .............................. 2002-001226
Jun. 18, 2002 (JP) .............................. 2002-176948
Jun. 18, 2002 (JP) .............................. 2002-176949
Jun. 18, 2002 (JP) .............................. 2002-176950
Jun. 24, 2002 (JP) .............................. 2002-182395

(51) Int. Cl.
*C07F 17/02* (2006.01)
*C23C 16/00* (2006.01)

(52) U.S. Cl. ...................................... 556/136; 427/252

(58) Field of Classification Search ................ 556/136; 427/252

See application file for complete search history.

(56) References Cited

U.S. PATENT DOCUMENTS

| | | | |
|---|---|---|---|
| 3,306,917 A | 2/1967 | Shapiro et al. | 260/429 |
| 5,770,752 A | 6/1998 | Kaufmann et al. | 556/11 |
| 6,207,232 B1 * | 3/2001 | Kadokura | 427/252 |
| 2001/0036509 A1 | 11/2001 | Kitada et al. | 427/255.28 |
| 2001/0050391 A1 | 12/2001 | Matsuno et al. | 257/306 |
| 2002/0161253 A1 * | 10/2002 | Voll et al. | 556/143 |

FOREIGN PATENT DOCUMENTS

| | | |
|---|---|---|
| JP | 2001/234347 | 8/2001 |
| WO | 01/42261 | 6/2001 |
| WO | 02/088152 | 11/2002 |

OTHER PUBLICATIONS

P.C. Liao, et al., "Characterization of $RuO_2$ thin films deposited on Si by metal-organic chemical vapor deposition", Thin Solid Films, vol. 287, pp. 74-79, 1996.

Tomonori Aoyama, et al., "Chemical vapor deposition of Ru and its application in (Ba, Sr)$TiO_3$ capacitors for future dynamic random access memories", Japanese Journal of Applied Physics, vol. 38, part 1, No. 4B, pp. 2194-2199, 1999.

Kadoshima, et al., Preliminary Manuscript of the $47^{th}$ Lecture of the Japanese Society of Applied Physics, p. 515 2000(with partial English translation).

G.D. Flesch, et al., "Ionization efficiency data and fragmentation mechanisms for ferrocene nickelocene, and ruthenocene", J.C.S. Dalton, pp. 1102-1105, 1972.

* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

Bis(cyclopentadienyl)ruthenium complex havimg a content of at least one member selected from among sodium, potassium, calcium, iron, nickel and zinc of 5 ppm or below; and bis(cyclopentadienyl)ruthenium complex incorporated with 10 to 100 ppm of rhenium The complexes are suitable for metalorganic chemical vapor deposition (MOCVD) and can give ruthenium-containing thin film.

14 Claims, 7 Drawing Sheets

RUTHENIUM COMPOUNDS, PROCESS FOR THEIR PREPARATION, AND RUTHENIUM-CONTAINING THIN FILMS MADE BY USING THE COMPOUNDS

TECHNICAL FIELD

The present invention relates to a ruthenium compound which is suited for use in a metal organic chemical vapor deposition (hereinafter referred to as MOCVD) method and to a method of producing the same, and relates to a ruthenium-containing thin film producing using the compound. More particularly, the present invention relates to a ruthenium compound which is best suited for use in a MOCVD method that employs a solid sublimation method, and to a method of producing the same, and relates to a ruthenium-containing thin film producing using the compound.

BACKGROUND ART

With recent rapid tends to high integration density of DRAM (Dynamic Random Access Memory) used as main memories of personal computers and work stations, there have been intensively developed dielectric and electrode materials which can realize a high integration density.

To impart predetermined dielectric characteristics to dielectric materials, a crystallization heat treatment under an oxidative atmosphere is necessary. Polysilicon, tungsten and titanium nitride have conventionally been used as the material for electrodes which is laminated with a dielectric substance. However, since the electrode is oxidized when subjected to a heat treatment at high temperature under an oxygen atmosphere, the electrode is inferior in heat resistance. Thus, intense interest has shown towards Pt which is less likely to react with oxygen at high melting point, and Ru, $RuO_2$, Ir and $IrO_2$ which maintain excellent electrical conductivity even when oxidized. In the formation of a film of Ru or $RuO_2$, a sputtering method is often used. For fine working required with higher integration density, a MOCVD method has been researched.

As the MOCVD material containing Ru, for example, cyclopentadiene materials such as bis(cyclopentadienyl)ruthenium (hereinafter referred to as $Ru(Cp)_2$) complex and bisethylcyclopentadienyl ruthenium (hereinafter referred to as $Ru(EtCp)_2$ complex, and β-diketone materials such as tris-2,2,6,6-tetramethyl-3,5-heptadionate ruthenium (hereinafter referred to as $Ru(DPM)_3$) complex are used.

Among these materials, the $Ru(DPM)_3$ complex is not often used as the MOCVD feedstock because its vapor pressure is lower than that of the $Ru(Cp)_2$ complex and $Ru(EtCp)_2$ complex. The $Ru(EtCp)_2$ complex has such advantages that a conventional film forming apparatus can be employed because it exists in the form of liquid at about room temperature, and the feedstock can be fed in a stable manner because its flow rate can be controlled by a conventional mass flow controller. However, the $Ru(EtCp)_2$ complex is not easily handled because it is unstable in air. Since the $Ru(Cp)_2$ complex exists in the form of a solid at about room temperature and does not substantially dissolve in an organic solvent, it must be fed into a film forming chamber by a sublimation method and has problems such as increase in feed amount and poor stability. However, the $Ru(Cp)_2$ complex is easily handled because it is stable to an air.

Various studies on the formation of a film using a $Ru(Cp)_2$ complex by the MOCVD method are reported in P. C. Liao et al. Thin Solid Films, 287, pp. 74–79 (1996), Aoyama et al. Jpn. J. Appl. Physics, 38, pp. 2194–2199 (1999), Kadoshima et al. Preliminary Manuscript of the 47th Lecture of The Japanese Society of Applied Physics, pp. 515, and Moto et al. Japanese Patent Application, First Publication No. 2001-234347. According to these studies, Ru and $RuO_2$ films having excellent characteristics are formed by the MOCVD method that employs a solid sublimation method.

However, the principal object of the above studies on the formation of a film using the $Ru(Cp)_2$ complex by the MOCVD method is to evaluate characteristics and the film forming method of Ru and $RuO_2$ films, and there is no description about an influence of the content of impurities in the $Ru(Cp)_2$ complex as the feedstock on the film formation.

DISCLOSURE OF INVENTION

A. Re: Influence of Impurities on Vaporization Characteristics

The $Ru(Cp)_2$ complex obtained by a conventional method contains substantial amounts of impurities such as sodium, potassium, calcium, iron, nickel, and zinc. The present inventors have found that vaporization characteristics of the $Ru(Cp)_2$ complex deteriorate when the $Ru(Cp)_2$ complex contains a large amount of impurities (for example, sodium, potassium, calcium, iron, nickel, and zinc).

The chemical form of the aforementioned impurities contained in the $Ru(Cp)_2$ complex is unclear; however, it is believed that vaporization characteristics deteriorate for the following reasons (1) to (4).

(1) In the Case in which Impurities Comprise Sodium or Potassium

Because it is known that a compound of sodium or potassium with cyclopentadiene (hereinafter referred to as Cp), NaCp or KCp, has very high reactivity, in the case in which the $Ru(Cp)_2$ complex contains a large amount of sodium or potassium, compounds such as NaCp and KCp as well as composites of these compounds with Ru are formed when the complex is stored in heat and, furthermore, the composites are altered during storage in heat and thus the $Ru(Cp)_2$ complex is altered by the action of the altered substance, therefore, it is believed that vaporization characteristics of the $Ru(Cp)_2$ complex deteriorate.

(2) In the Case in which Impurities Comprise Calcium

Because it is presumed that $Ca(Cp)_2$, which is a composite of calcium and Cp, is unstable as compared with $Ru(Cp)_2$, in the case in which the $Ru(Cp)_2$ complex contains a large amount of calcium, a $Ca(Cp)_2$ composite is formed when the complex is stored in heat and this complex causes an interaction with Cp of the $Ru(Cp)_2$ complex during storage in heat and thus the $Ru(Cp)_2$ complex is altered, therefore, it is believed that vaporization characteristics of the $Ru(Cp)_2$ complex deteriorate. Furthermore, in the case of Ca, a Cp complex thereof has a large vapor pressure as compared with Na and K, and therefore, it may well be that Ca is incorporated into the film after the vaporization of the Cp complex.

(3) In the Case in which Impurities Comprise Iron or Nickel

It has been reported that $Fe(Cp)_2$, which is a composite of iron or nickel with Cp, exhibits a weak binding energy between metal and Cp as compared with $Ru(Cp)_2$ (J. Chem. Soc., Dalton trans. (1972), pp. 1102–1105). It is believed that, since the binding energy between iron and Cp and the binding energy between nickel and Cp are smaller than the binding energy between ruthenium and Cp, $Fe(Cp)_2$ and $Ni(Cp)_2$ are decomposed during storage in heat and a large amount of the existing $Ru(Cp)_2$ is altered by a catalytic action of the decomposition product, therefore, it is believed that vaporization characteristics of the Ru(Cp)$_2$ complex deteriorate.

(4) In the Case in which Impurities Comprise Zinc

It is not clear whether or not zinc, which exists as impurities in the Ru(Cp)$_2$ complex, and Cp form a complex or takes the form like a chloride; however, it is believed that a composite of zinc with Cp or chlorine, or free Cp or chlorine causes an interaction with Cp of Ru(Cp)$_2$ during storage in heat, thereby causing alteration of Ru(Cp)$_2$, therefore, it is believed that vaporization characteristics of the Ru(Cp)$_2$ complex deteriorate.

B. Re: Influence of Impurities on Film Forming Rate

Taking account of an influence of impurities on the film forming rate, means for obtaining a proper film forming rate has been required.

In light of the above problems, a first object of the present invention relating to A (1) is to provide a ruthenium compound wherein good vaporization characteristics can be obtained by avoiding deterioration of vaporization characteristics caused by impurities such as sodium and potassium using the MOCVD method that employs a solid sublimation method.

A second object of the present invention relating to A (2) is to provide a ruthenium compound for a MOCVD method, which can suppress decrease of vaporization characteristics caused by impurities such as calcium.

A third object of the present invention relating to A (3) is to provide a ruthenium compound which can suppress decrease of vaporization characteristics caused by impurities such as iron and nickel.

A fourth object of the present invention relating to A (4) is to provide a ruthenium compound which can suppress decrease of vaporization characteristics caused by impurities such as zinc.

A fifth object of the present invention relating to B is to provide a ruthenium compound for a MOCVD method, which is capable of obtaining a proper film forming rate by the MOCVD method that employs a solid sublimation method.

Another object of the present invention is to provide a ruthenium-containing thin film, which is excellent in step coverage and surface morphology and is also excellent in electrical characteristics, by achieving at least one of the above first to fifth objects.

The ruthenium compound according to the first embodiment of the present invention is directed to an improvement of a ruthenium compound comprising a Ru(Cp)$_2$ complex and is characterized in that the content of either or both of sodium and potassium in the compound is 5 ppm or less. According to the ruthenium compound, by controlling the content of either or both of sodium and potassium in the compound to the specific numerical value within the above range, it is made possible that either or both of sodium and potassium and Cp may hardly form compounds or composites of these compounds with Ru upon formation of a ruthenium-containing thin film, therefore, deterioration of vaporization characteristics of the Ru(Cp)$_2$ complex caused by the composite can be suppressed. As described above, since the ruthenium compound wherein the content of impurities is controlled has good vaporization characteristics in the MOCVD method that employs a solid sublimation method, a uniform ruthenium-containing thin film is obtained. Therefore, the resulting ruthenium-containing thin film is excellent in step coverage and surface morphology and is also excellent in electrical characteristics.

As shown in FIG. 1, the method of producing a ruthenium compound according to the first embodiment of the present invention is directed to an improvement of a method of producing a ruthenium compound, which comprises the step 11 of obtaining a crude product of a Ru(Cp)$_2$ complex using a ruthenium-containing compound and Cp, and the step 12 of sublimating the resulting crude product to collect a purified product. The method is characterized in that a sublimate obtained by sublimation of the crude product is passed through a deposition inhibitor to remove either or both of sodium and potassium in the case of collecting the sublimate during the sublimation and collection step 12. According to the method of producing a ruthenium compound, by passing the sublimate through the deposition inhibitor during the sublimation and collection step 12, the content of either or both of sodium and potassium in the Ru(Cp)$_2$ complex is effectively decreased.

The ruthenium-containing thin film according to the first embodiment of the present invention is formed by using the ruthenium compound of the first embodiment or the ruthenium compound obtained by the method of producing a ruthenium compound of the first embodiment. According to the ruthenium-containing thin film, since the ruthenium compound of the first embodiment or the ruthenium compound obtained by the method of producing a ruthenium compound of the first embodiment has good vaporization characteristics in the MOCVD method that employs a solid sublimation method, a uniform ruthenium-containing thin film is obtained. Therefore, the resulting ruthenium-containing thin film is excellent in step coverage and surface morphology and is also excellent in electrical characteristics.

As described above, according to the ruthenium compound of the first embodiment, and the method of producing the same and the ruthenium-containing thin film obtained from the compound, the first object of the present invention can be achieved.

The ruthenium compound according to the second embodiment of the present invention is directed to an improvement of a ruthenium compound comprising a Ru(Cp)$_2$ complex and is characterized in that the content of calcium in the compound is 5 ppm or less. According to the ruthenium compound, by controlling the content of calcium in the compound to the specific numerical value within the above range, it is made possible that calcium and Cp may hardly form a composite upon formation of a ruthenium-containing thin film, therefore, deterioration of vaporization characteristics of the Ru(Cp)$_2$ complex caused by the composite can be suppressed. Furthermore, incorporation of Ca into the Ru-containing thin film can be prevented. As described above, since the ruthenium compound wherein the content of impurities is controlled has good vaporization characteristics in the MOCVD method that employs a solid sublimation method, a uniform ruthenium-containing thin film is obtained. Therefore, the resulting ruthenium-containing thin film is excellent in step coverage and surface morphology and is also excellent in electrical characteristics.

As shown in FIG. 4, the method of producing a ruthenium compound according to the second embodiment of the present invention is directed to an improvement of a method of producing a ruthenium compound, which comprises a step 111 of obtaining a crude product of a Ru(Cp)$_2$ complex using a ruthenium-containing compound and Cp, a step 112 of sublimating the resulting crude product to obtain a purified product and a step 114 of recrystallizing the purified product. The method is characterized in that it further comprises a step 113 of dissolving in a soluvent the purified product and filtering the dissolved solution after the sublimation step 112 in place of the step of performing the column purification and recrystallization, and tetrahydrofuran (hereinafter referred to as THF) is used as a solvent in the filtration step 113. According to the method of producing a ruthenium compound, by recrystallizing using THF as the solvent, THF highly dissolves impurities as compared with an n-pentane solvent which has conventionally been used for recrystallization, and thus the amount of calcium as impurities after recrystallization can be considerably decreased. By providing the filtration step 113 using THF having a large solubility to the $Ru(Cp)_2$ complex, the amount of the $Ru(Cp)_2$ complex to be treated can be increased as compared with a treating step using a conventional column, and thus productive efficiency is also improved.

The ruthenium-containing thin film according to the second embodiment of the present invention is formed by using the ruthenium compound of the second embodiment or the ruthenium compound obtained by the method of producing a ruthenium compound of the second embodiment. According to the ruthenium-containing thin film, since deterioration of vaporization characteristics of the ruthenium compound is suppressed, a uniform ruthenium-containing thin film is obtained. Also contamination with Ca can be prevented. Therefore, the resulting ruthenium-containing thin film is excellent in step coverage and surface morphology and is also excellent in electrical characteristics.

As described above, according to the ruthenium compound of the second embodiment, and the method of producing the same and the ruthenium-containing thin film obtained from the compound, the second object of the present invention can be achieved.

The ruthenium compound according to the third embodiment of the present invention is directed to an improvement of a ruthenium compound comprising a $Ru(Cp)_2$ complex and is characterized in that the content of either or both of iron and nickel in the compound is 5 ppm or less. According to the ruthenium compound, by controlling the content of either or both of iron and nickel in the compound to the specific numerical value within the above range, it is made possible for either or both of iron and nickel to not significantly form composites of iron and nickel with Cp upon formation of a ruthenium-containing thin film, therefore, deterioration of vaporization characteristics of the $Ru(Cp)_2$ complex caused by the composite can be suppressed. As described above, since the ruthenium compound wherein the content of impurities is controlled has good vaporization characteristics in the MOCVD method that employs a solid sublimation method, a uniform ruthenium-containing thin film is obtained. Therefore, the resulting ruthenium-containing thin film is excellent in step coverage and surface morphology and is also excellent in electrical characteristics.

As shown in FIG. 5, the method of producing a ruthenium compound according to the third embodiment of the present invention is directed to an improvement of a method of producing a ruthenium compound, which comprises a step 211 of obtaining a crude product of a $Ru(Cp)_2$ complex using a ruthenium-containing compound and Cp, a step 212 of sublimating the crude product to obtain a purified product of the complex, and a step 213 of dissolving the purified product in a solvent and repurifying the solution by passing it through a column. The method is characterized in that the eluent used in the alumina column purification step 213 is a mixed solvent obtained by adding 10 to 30 mol % of dichloromethane to 90 to 70 mol % of benzene. According to the method of producing a ruthenium compound, when the eluent used in the column purification step 213 is a mixed solvent having a controlled polarity suited to remove iron or nickel obtained by adding 10 to 30 mol % of dichloromethane to 90 to 70 mol % of benzene, the eluent having a controlled polarity so as to greatly dissolve iron or nickel as compared with a non-polar solvent comprising benzene, which has conventionally used as the eluent of the column, and thus the amount of iron or nickel as impurities after recrystallization can be considerably decreased.

The ruthenium-containing thin film according to the third embodiment of the present invention is formed by using the ruthenium compound of the third embodiment or the ruthenium compound obtained by the method of producing a ruthenium compound of the third embodiment. According to the ruthenium-containing thin film, since the ruthenium compound of the third embodiment or the ruthenium compound obtained by the method of producing a ruthenium compound of the third embodiment is a ruthenium compound wherein deterioration of vaporization characteristics are suppressed, a uniform ruthenium-containing thin film is obtained. Therefore, the resulting ruthenium-containing thin film is excellent in step coverage and surface morphology and is also excellent in electrical characteristics.

As described above, according to the ruthenium compound of the third embodiment, and the method of producing the same and the ruthenium-containing thin film obtained from the compound, the third object of the present invention can be achieved.

The ruthenium compound according to the fourth embodiment of the present invention is directed to an improvement of a ruthenium compound comprising a $Ru(Cp)_2$ complex and is characterized in that the content of zinc in the compound is 5 ppm or less. According to the ruthenium compound, by controlling the content of zinc in the compound to the specific numerical value within the above range, it is made possible for composites of zinc with Cp or chlorine, or free Cp or chlorine to not substantially cause an interaction with Cp of $Ru(Cp)_2$ during storage in heat upon formation of a ruthenium-containing thin film, therefore, deterioration of vaporization characteristics of the $Ru(Cp)_2$ complex can be suppressed. As described above, since the ruthenium compound wherein the content of impurities is controlled has good vaporization characteristics in the MOCVD method that employs a solid sublimation method, a uniform ruthenium-containing thin film is obtained. Therefore, the resulting ruthenium-containing thin film is excellent in step coverage and surface morphology and is also excellent in electrical characteristics.

As shown in FIG. 6, the method of producing a ruthenium compound according to the fourth embodiment of the present invention is directed to an improvement of a method of producing a ruthenium compound, which comprises a step 311 of obtaining a crude product of a $Ru(Cp)_2$ complex using a ruthenium-containing compound and Cp, a step 312 of filtering a solution containing the resulting crude product, a step 313 of extracting the crude product collected by filtration with a solvent, a step 314 of purifying a solution containing the extracted crude product by passing the solution through an alumina column, and a step 315 of recrystallizing a solution containing the crude product. The method is characterized in that the solvent used in the extraction step 313 is a mixed solvent containing tetrahydrofuran (hereinafter referred to as THF) and n-pentane, and the weight ratio of tetrahydrofuran to n-pentane in the mixed solvent (THF/n-pentane) is from 5/5 to 2/8. According to the method of producing a ruthenium compound, when the solvent used in the extraction step 313 is a mixed solvent containing THF and n-pentane and the weight ratio of THF to n-pentane (THF/n-pentane) is controlled with a range from 5/5 to 2/8, the mixed solvent highly dissolves the zinc compound as compared with an n-pentane solvent which has been conventionally used as the eluent and polarity between alumina, which is a filler of the alumina column, and the solvent is suitable, therefore the amount of zinc as impurities after passing through the alumina column can be considerably decreased.

The ruthenium-containing thin film according to the fourth embodiment of the present invention is formed by using the ruthenium compound of the fourth embodiment or the ruthenium compound obtained by the method of producing a ruthenium compound of the fourth embodiment. According to the ruthenium-containing thin film, since the ruthenium compound of the fourth embodiment or the ruthenium compound obtained by the method of producing a ruthenium compound of the fourth embodiment is a ruthenium compound wherein deterioration of vaporization characteristics are suppressed, a uniform ruthenium-containing thin film is obtained. Therefore, the resulting ruthenium-containing thin film is excellent in step coverage and surface morphology and is also excellent in electrical characteristics.

As described above, according to the ruthenium compound of the fourth embodiment, and the method of producing the same and the ruthenium-containing thin film obtained from the compound, the fourth object of the present invention can be achieved.

The ruthenium compound according to the fifth embodiment of the present invention is a ruthenium compound comprising a bis(cyclopentadienyl)ruthenium complex, wherein the content of rhenium in the compound is from 10 to 100 ppm. According to the ruthenium compound, by controlling the content of rhenium to the specific numerical value within the above range, a given amount of a nucleus required for the growth of the film is formed by rhenium on formation of a ruthenium-containing thin film, and thus a proper film forming rate can be realized.

The ruthenium-containing thin film according to the fifth embodiment of the present invention is formed by using the ruthenium compound of the fifth embodiment. Since a film is formed by using a ruthenium compound which enables a proper film forming rate, the resulting ruthenium-containing thin film is a uniform ruthenium-containing thin film.

As described above, according to the ruthenium compound of the fifth embodiment and the ruthenium-containing thin film obtained from the compound, the fifth object of the present invention can be achieved.

BEST MODE FOR CARRYING OUT THE INVENTION

Preferred embodiments of the present invention will be described with reference to the accompanying drawings. The present invention is not limited to the following embodiments and constituent features of the embodiments may be appropriately combined.

FIRST EMBODIMENT

The present inventors have intensively researched the influence of impurities contained in a ruthenium compound on the film formation using the MOCVD method and confirmed that a proper film forming rate can be realized by optimizing the content of either or both of sodium and potassium among impurities contained in the ruthenium compound.

The ruthenium compound of the present invention is a ruthenium compound comprising a $Ru(Cp)_2$ complex, wherein the content of either or both of sodium and potassium in the compound is 5 ppm or less. When the content of impurities exceeds 5 ppm, vaporization characteristics deteriorate. The content of impurities is preferably from 0 to 3 ppm, more preferably from 0 to 2 ppm, and still more preferably from 0 to 1.5 ppm.

The method of producing a ruthenium compound of the present invention will now be described.

Figure 1:
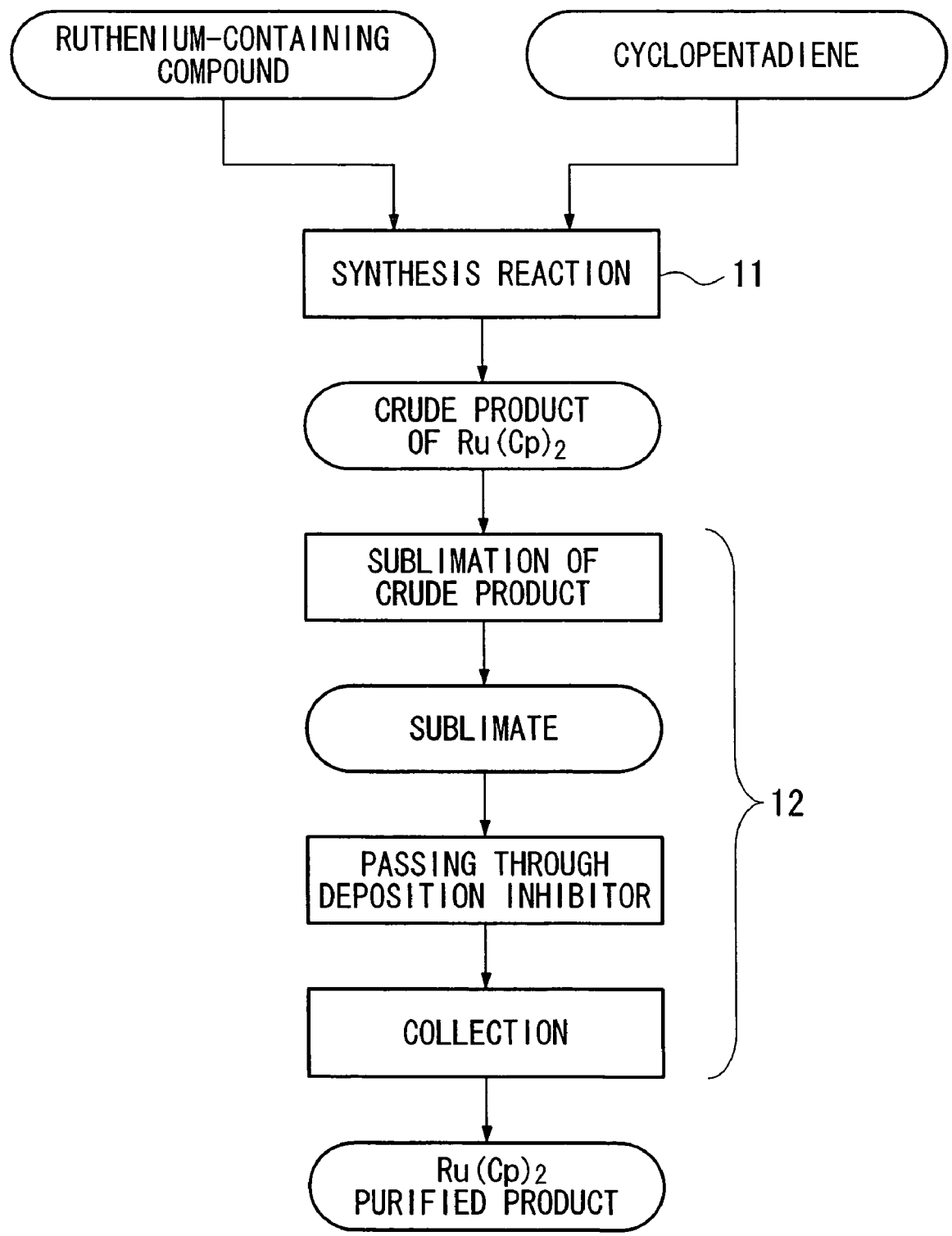
FIG. 1 is a flow chart showing the respective steps of a method of producing a ruthenium compound according to the first embodiment of the present invention.

First, as shown in FIG. 1, a crude product of a $Ru(Cp)_2$ complex is obtained by using a ruthenium-containing compound and Cp (step 11). In this step 11, a crude product of a $Ru(Cp)_2$ complex is obtained by a synthesis method which has conventionally been performed.

In the first solvent, ruthenium chloride hydrate $RuCl_3 \cdot nH_2O$ is dissolved. Examples of the first solvent include alcohols such as ethanol, isopropanol, and methanol. The reaction shown in the following scheme (1) is performed by adding Cp to the solution and further adding a metallic zinc powder.

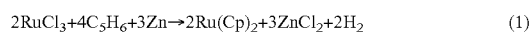
$$2RuCl_3 + 4C_5H_6 + 3Zn \rightarrow 2Ru(Cp)_2 + 3ZnCl_2 + 2H_2 \qquad (1)$$

After filtering the reaction solution to remove the first solvent and zinc chloride dissolved in the solvent, the reaction product collected by filtration is extracted by dissolving in the second solvent. Examples of the second solvent include tetrahydrofuran, benzene, and n-pentane. A crude product of a $Ru(Cp)_2$ complex is obtained by removing the second solvent from the extract.

A crude product of a $Ru(Cp)_2$ complex may also be synthesized by using the method described in Organic synthesis, pp. 96–98 (1961). According to the method described in the above document, sodium is suspended in 1,2-dimethoxyethane and Cp is added dropwise in the suspension, thereby to dissolve sodium. In this case, the reaction shown in the following scheme (2) arises.

$$2C_5H_6 + 2Na \rightarrow 2C_5H_5^-Na^+ + H_2 \qquad (2)$$

When evolution of hydrogen is completed by the reaction between Cp and sodium, the mixed solution is maintained at a temperature which is slightly lower than the reflux temperature. When the entire sodium is not dissolved, the solution is cooled to room temperature and several ml of Cp is added, and then the mixed solution is heated again until sodium is completely dissolved. After the completion of the reaction shown in the scheme (2), ruthenium trichloride and metallic ruthenium are added to the mixed solution and, after maintaining at the temperature which is slightly lower than the reflux temperature, the mixture is reacted by heating with stirring under a nitrogen atmosphere. In this case, the reaction is shown in the following scheme (3).

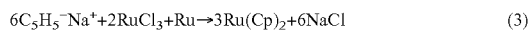
$$6C_5H_5^-Na^+ + 2RuCl_3 + Ru \rightarrow 3Ru(Cp)_2 + 6NaCl \qquad (3)$$

After the completion of the reaction shown in the scheme (3), the solvent is removed while stirring using an aspirator to obtain a crude product of a $Ru(Cp)_2$ complex.

While the above two kinds of synthesis reactions were described as the reaction for obtaining the crude product of the step 11 in this embodiment, the reaction is not limited to these synthesis reactions.

Next, the resulting crude product is sublimated to collect a purified product (step 12).

In this step 12, the crude product is sublimated by evacuation or heating, and then the sublimate is collected and purified.

The present invention is characterized in that a sublimate obtained by sublimation of the crude product is passed through a deposition inhibitor to remove either or both of sodium and potassium in the case of collecting the sublimate during the sublimation and collection step 12.

Before collecting the sublimate, the sublimate is passed through the deposition inhibitor to remove sodium and potassium components contained in the sublimate. When a purified product is obtained by collecting the sublimate without passing through the deposition inhibitor, the $Ru(Cp)_2$ complex contains sodium and potassium in an amount greater than the range defined in the present invention, while the content of sodium and potassium in the sublimate can be efficiently decreased by passing it through the deposition inhibitor. Examples of the deposition inhibitor include glass wool, silica gel, alumina, and activated carbon.

Figure 2:
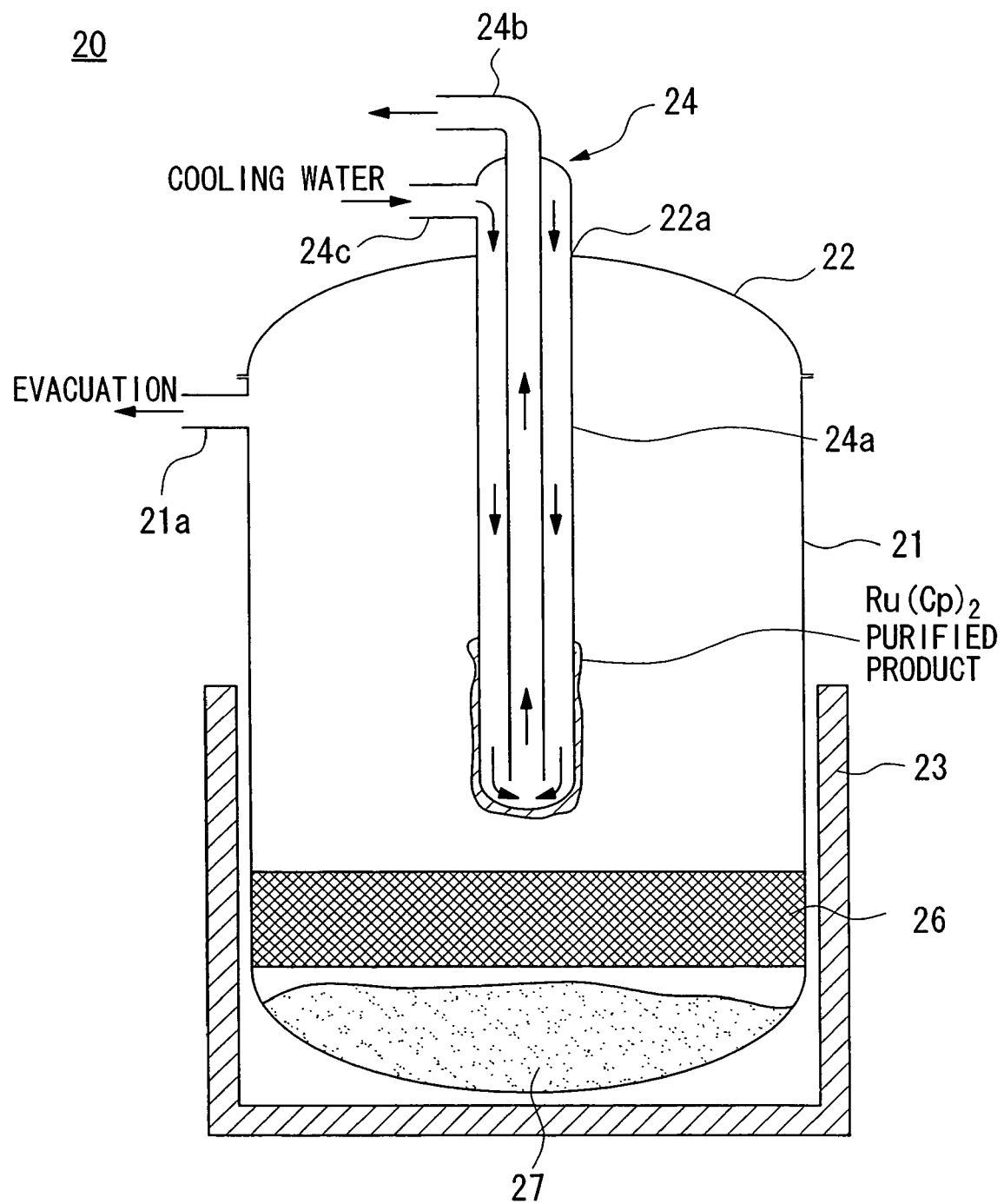
FIG. 2 is an explanatory drawing of an apparatus used in the sublimation and collection step of the present invention.

This step 12 is performed by using an apparatus shown in FIG. 2.

This apparatus 20 comprises a closed-end cylindrical vessel 21 and a cap 22 for sealing the vessel. Outside the vessel, a heater 23 for heating the vessel is provided. A purified product collecting pipe 24 having a double tubular structure pierces through a center hole 22a of the cap and faces on the inside of the vessel. At the upper portion of the side wall of the vessel 21, a vacuum port 21a for evacuating the vessel is provided. The purified product collecting pipe 24 comprises an outer pipe 24a and an inner pipe 24b in the center of the outer pipe, and the inner pipe pierces through the top portion of the outer pipe. At the side portion of the outer pipe, which projects out from the center hole 22a of the cap, a cooling water inlet 24c is provided. A deposition inhibitor 26 is provided between the lower end of the outer pipe 24a in the vessel and the inner bottom of the vessel 21.

The method of sublimating the resulting crude product and collecting the sublimate using the apparatus 20 with such a constitution will now be described.

First, a crude product $Ru(Cp)_2$ 27 obtained in the step 11 is charged in the bottom of the vessel. Then, a deposition inhibitor 26 is fixed to the inside of the vessel and the vessel 21 is sealed using a cap 22 with a purified product collecting pipe 24 to form an airtight state in the vessel. The vessel is evacuated by evacuating air through the vacuum port 21a and the bottom of the vessel is heated by the heater 23. Cooling water is introduced through the inlet 24c to cool the entire outer pipe 24a, and is then discharged from the bottom of the inner pipe 24b through the inner pipe 24b. The crude product $Ru(Cp)_2$ 27 is heated by the heater 23 and the crude product $Ru(Cp)_2$ is sublimated. The sublimated $Ru(Cp)_2$ passes through the deposition inhibitor 26, and thus the component of impurities such as sodium and potassium in the sublimate is removed. After removing the component of impurities, the sublimate is deposited on the periphery of the outer pipe 24a cooled with cooling water and then collected as a solid purified product $Ru(Cp)_2$.

As described above, by passing through the steps 11 and 12, it is made possible to obtain a $Ru(Cp)_2$ complex wherein the content of either or both of sodium and potassium is 5 ppm or less, which is a ruthenium compound of the present invention.

Figure 3:
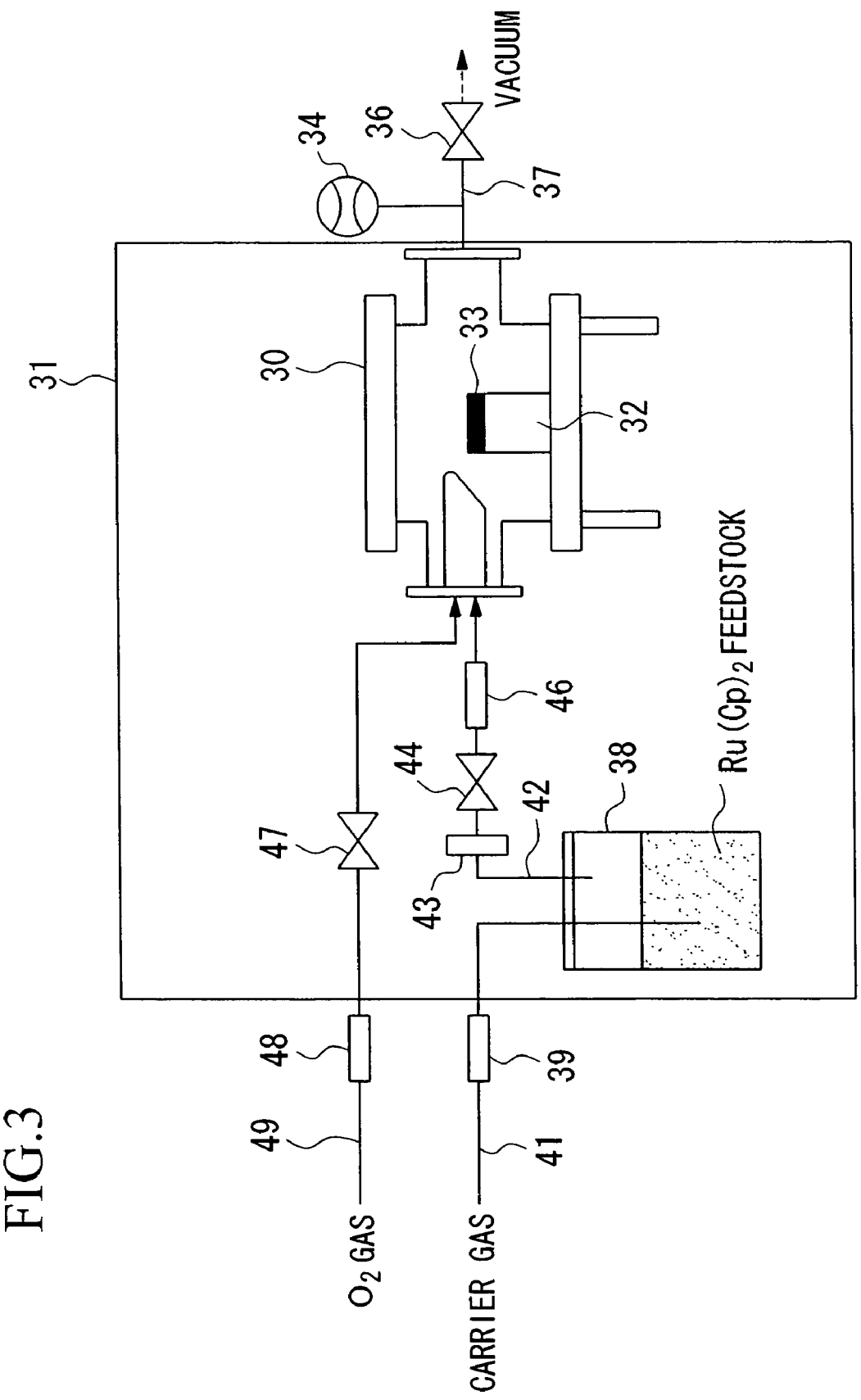
FIG. 3 is a schematic view of a MOCVD apparatus that employs a solid sublimation method.

As shown in FIG. 3, a MOCVD apparatus that employs a solid sublimation method comprises a film forming chamber 30, the entire apparatus being covered with a heating apparatus 31. In the film forming chamber 30, a heater 32 is provided and a substrate 33 is held on the heater 32. The film forming chamber 30 is evacuated through a piping 37 equipped with a pressure gauge 34 and a needle valve 36. The heating apparatus 31 is provided with a feedstock tank 38 and a $Ru(Cp)_2$ complex which is solid at normal temperature, the content of either or both of sodium and potassium being controlled to 5 ppm or less, is stored in the feedstock tank 38. A carrier gas inlet pipe 41 is connected to the feedstock tank 38 via a gas flow controller 39, and a feed pipe 42 is connected to the feedstock tank 38. The feed pipe 42 is provided with a filter 43, a needle valve 44 and a gas flow controller 46, and the feed pipe 42 is connected to the film forming chamber 30. To the film forming chamber 30, an oxygen gas inlet pipe 49 is connected via a needle valve 47 and a gas flow controller 48.

In this apparatus, the feedstock tank 38 is heated to about 180° C. by the heating apparatus 31 and the $Ru(Cp)_2$ complex stored in the tank 38 is gradually sublimated. A carrier gas is introduced into the feedstock tank 38 through the inlet pipe 41 and the $Ru(Cp)_2$ complex sublimated in the feedstock tank 38 is transferred to the film forming chamber 30 through the feed pipe 42. Examples of the carrier gas include argon, helium and nitrogen gases. An oxygen gas is fed into the film forming chamber 30 through the oxygen gas inlet pipe 49. In the film forming chamber 30, vapor of the $Ru(Cp)_2$ complex is thermally decomposed together with oxygen and Ru or $RuO_2$ thus formed is deposited on a substrate 33. Consequently, a uniform ruthenium-containing thin film is formed.

EXAMPLES

Examples of this embodiment will be described in detail, together with Comparative Examples.

Example 1-1

A $Ru(Cp)_2$ complex having a sodium content of 1.4 ppm produced by using a deposition inhibitor made of a glass wool was sealed in an ampule bottle under an argon atmosphere. The ampule bottle was heated to 200° C. by a heating furnace and then maintained at the same temperature for 72 hours. The ampule bottle was taken out from the heating furnace and air-cooled to room temperature. Vaporization characteristics of the ruthenium compound cooled to room temperature in the ampule bottle were measured by using a TG-DTA apparatus (manufactured by MAC-Science Co.). The measuring conditions by the TG-DTA apparatus are shown in Table 1.

TABLE 1

| Temperature | 25° C.–500° C. (Heating rate: 10° C./min) |
|---|---|
| Pressure | 101.3 kPa |
| Carrier gas (Ar) flow rate | 100 sccm |
| Measuring cell | made of alumina |
| Measuring apparatus | TGA-2000, manufactured by MAC-Science Co. |

Example 1-2

In the same manner as in Example 1-1, except for using a Ru(Cp)$_2$ complex having a potassium content of 1.7 ppm produced by using a deposition inhibitor made of a glass wool, vaporization characteristics were measured by the TG-DTA apparatus.

Comparative Example 1-1

In the same manner as in Example 1-1, except for using a Ru(Cp)$_2$ complex having a potassium content of 6.0 ppm produced without using a deposition inhibitor, vaporization characteristics were measured by the TG-DTA apparatus.

Comparative Example 1-2

In the same manner as in Example 1-1, except for using a Ru(Cp)$_2$ complex having a potassium content of 6.3 ppm produced without using a deposition inhibitor, vaporization characteristics were measured by the TG-DTA apparatus.

<Comparison Test and Evaluation>

The vaporization amount of the ruthenium compounds obtained in Examples 1-1 and 1-2 and Comparative Examples 1-1 and 1-2 was measured at 150° C. using a TG-DTA apparatus. The results are shown in Table 2.

TABLE 2

| | Impurities and content (ppm) | | Vaporization amount (% by weight) |
|---|---|---|---|
| Example 1-1 | Na | 1.4 | 4.6 |
| Example 1-2 | K | 1.7 | 4.8 |
| Comparative Example 1-1 | Na | 6.0 | 8.5 |
| Comparative Example 1-2 | K | 6.3 | 7.9 |

As is apparent from Table 2, in Comparative Examples 1-1 and 1-2 wherein the content of impurities in the Ru(Cp)$_2$ complex exceeds 5 ppm, the vaporization amount at 150° C. increased as compared with Example 1-1 and 1-2. The Ru(Cp)$_2$ complex is hardly vaporized because of its low vapor pressure at a temperature of about 150° C. A large vaporization amount at this temperature means that the complex contains a large amount of impurities which are easily vaporized. As a result, it has been found that vaporization characteristics of the Ru(Cp)$_2$ complex containing impurities in the amount greater than the range defined in the present invention deteriorate after storage at high temperature. A large vaporization amount under the conditions of the temperature lower than the temperature at which the Ru(Cp)$_2$ complex is vaporized means that considerable vaporization is caused by the component other than the Ru(Cp)$_2$ complex. This exerts an adverse influence on properties of the film in the case of forming a film by the MOCVD method. On the other hand, in Examples 1-1 and 1-2 of this embodiment wherein the content of impurities in the Ru(Cp)$_2$ complex is controlled within the range defined in the present invention, the vaporization amount decreases as compared with Comparative Examples 1-1 and 1-2. The reason is believed to be as follows. That is, deterioration of vaporization characteristics of the Ru(Cp)$_2$ complex was suppressed because of less composite made of sodium or potassium and Cp and less degree of alteration of the Ru(Cp)$_2$ complex caused by the composite.

SECOND EMBODIMENT

The present inventors have intensively researched on the influence of impurities contained in a ruthenium compound on the film formation using the MOCVD method and confirmed that characteristics of the ruthenium compound can be improved by optimizing the content of calcium among impurities contained in the ruthenium compound.

The ruthenium compound of the present invention is a ruthenium compound comprising a Ru(Cp)$_2$ complex, wherein the content of calcium in the compound is 5 ppm or less. When the content of impurities exceeds 5 ppm, characteristics of the Ru(Cp)$_2$ complex deteriorate. The content of impurities is preferably from 0 to 3 ppm, more preferably from 0 to 1 ppm, and still more preferably from 0 to 0.1 ppm.

The method of producing a ruthenium compound of the present invention will now be described.

Figure 4:
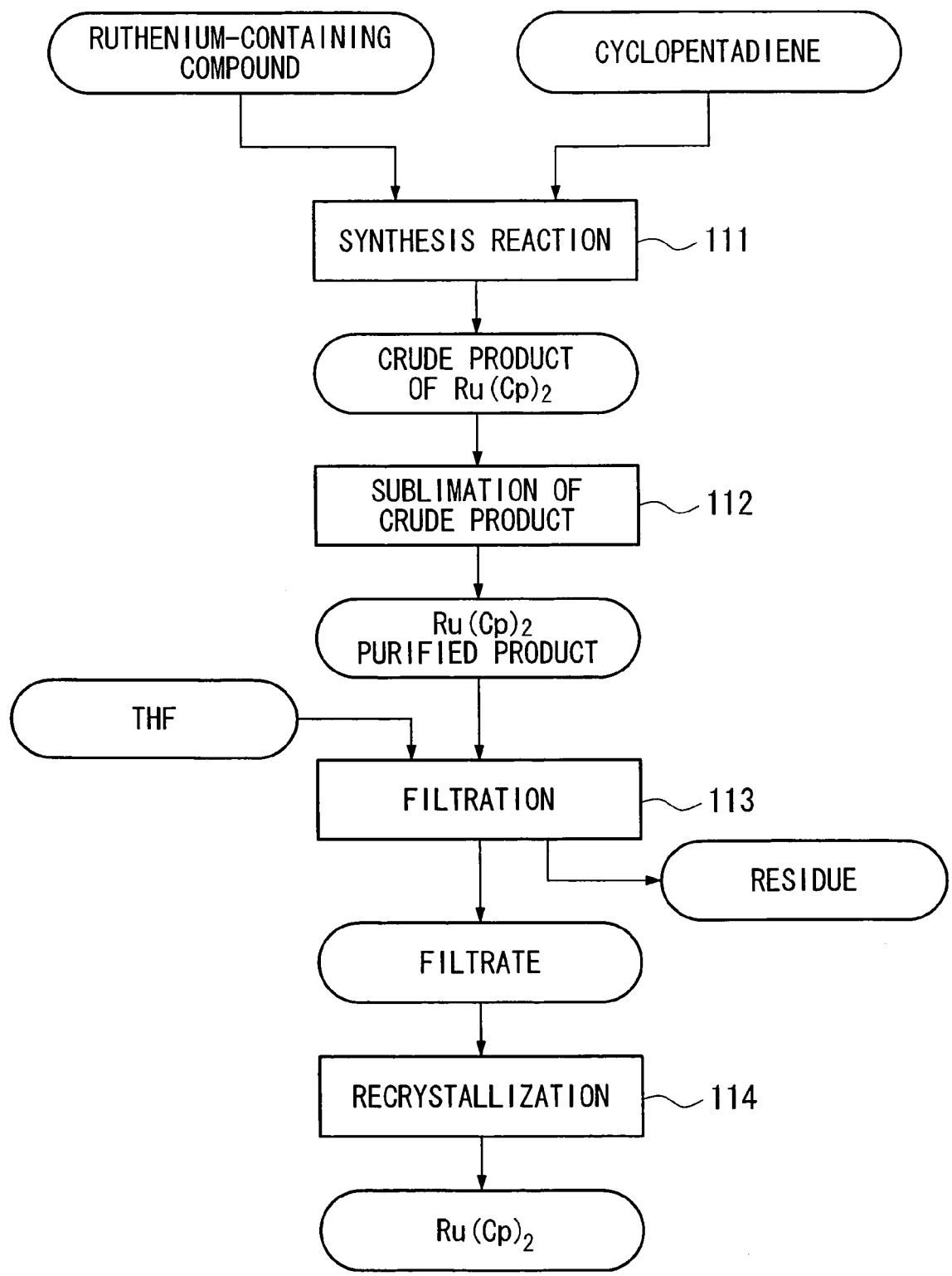
FIG. 4 is a flow chart showing the respective steps of a method of producing a ruthenium compound according to the second embodiment of the present invention.

First, as shown in FIG. 4, a crude product of a Ru(Cp)$_2$ complex is obtained by using a ruthenium-containing compound and Cp (step 111). In this step 111, a crude product of a Ru(Cp)$_2$ complex is obtained by a synthesis method which has conventionally been performed.

In the first solvent, ruthenium chloride hydrate RuCl$_3$.nH$_2$O is dissolved. Examples of the first solvent include alcohols such as ethanol, isopropanol, and methanol. The reaction shown in the following scheme (4) is performed by adding Cp to the solution and further adding a metallic zinc powder.

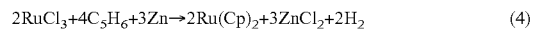

$$2RuCl_3 + 4C_5H_6 + 3Zn \rightarrow 2Ru(Cp)_2 + 3ZnCl_2 + 2H_2 \qquad (4)$$

After filtering the reaction solution to remove the first solvent and zinc chloride dissolved in the solvent, the reaction product collected by filtration is extracted by dissolving in the second solvent. Examples of the second solvent include tetrahydrofuran, benzene, and n-pentane. A crude product of a Ru(Cp)$_2$ complex is obtained by removing the second solvent from the extract.

A crude product of a Ru(Cp)$_2$ complex may also be synthesized by using the method described in Organic synthesis, pp. 96–98 (1961). According to the method described in the above document, sodium is suspended in 1,2-dimethoxyethane and Cp is added dropwise in the suspension, thereby to dissolve sodium. In this case, the reaction shown in the following scheme (5) arises.

$$2C_5H_6 + 2Na \rightarrow 2C_5H_5^-Na^+ + H_2 \qquad (5)$$

When evolution of hydrogen is completed by the reaction between Cp and sodium, the mixed solution is maintained at a temperature which is slightly lower than the reflux temperature. When the entirety of the sodium is not dissolved, the solution is cooled to room temperature and several ml of Cp is added, and then the mixed solution is heated again until sodium is completely dissolved. After the completion of the reaction shown in the scheme (5), ruthenium trichloride and metallic ruthenium are added to the mixed solution and, after maintaining at the temperature which is slightly lower than the reflux temperature, the mixture is reacted by heating with stirring under a nitrogen atmosphere. In this case, the reaction is shown in the following scheme (6).

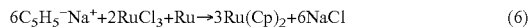

$$6C_5H_5^-Na^+ + 2RuCl_3 + Ru \rightarrow 3Ru(Cp)_2 + 6NaCl \quad (6)$$

After the completion of the reaction shown in the scheme (6), the solvent is removed while stirring using an aspirator to obtain a crude product of a $Ru(Cp)_2$ complex.

While the above two kinds of synthesis reactions were described as the reaction for obtaining the crude product of the step 111 in this embodiment, the reaction is not limited to these synthesis reactions.

Next, the resulting crude product is sublimated to obtain a purified product (step 112).

In this step 112, the crude product is sublimated by evacuation or heating, and then the sublimate is collected and purified.

Next, the purified product obtained in the sublimation step 112 is dissolved in a solvent and the solution is filtered (step 113).

Since the amount of the $Ru(Cp)_2$ complex to be treated can be increased by this step 113 as compared with the separation step using a column, which has conventionally been used, the productive efficiency is improved. In this case, THF is used as the solvent.

Furthermore, the filtrate obtained in the filtration step 113 is recrystallized (step 114).

In the recrystallization step 114, since THF used as the solvent in the filtration step 113 can greatly dissolve impurities as compared with an n-pentane solvent, which has conventionally been used for recrystallization, the amount of calcium as impurities after recrystallization can be considerably decreased. By using THF having a large solubility to the $Ru(Cp)_2$ complex, the amount of the $Ru(Cp)_2$ complex to be treated can be increased as compared with a treating step using a conventional column, and thus productive efficiency is also improved.

As described above, by passing through the steps 111 and 114, it is made possible to obtain a $Ru(Cp)_2$ complex wherein the content of calcium is 5 ppm or less, which is a ruthenium compound of the present invention.

The constitution of the MOCVD apparatus that employs a solid sublimation method of this embodiment is almost the same as that of the apparatus described with reference to FIG. 3 in the first embodiment, and the apparatus comprises a film forming chamber 30, the entire apparatus being covered with a heating apparatus 31. In the film forming chamber 30, a heater 32 is provided and a substrate 33 is held on the heater 32. The film forming chamber 30 is evacuated through a piping 37 equipped with a pressure gauge 34 and a needle valve 36. The heating apparatus 31 is provided with a feedstock tank 38 and, in this embodiment, a $Ru(Cp)_2$ complex which is solid at normal temperature, the content of calcium being controlled to 5 ppm or less, is stored in the feedstock tank 38. A carrier gas inlet pipe 41 is connected to the feedstock tank 38 via a gas flow controller 39, and a feed pipe 42 is connected to the feedstock tank 38. The feed pipe 42 is provided with a filter 43, a needle valve 34 and a gas flow controller 46, and the feed pipe 42 is connected to the film forming chamber 30. To the film forming chamber 30, an oxygen gas inlet pipe 49 is connected via a needle valve 47 and a gas flow controller 48.

In this apparatus, the feedstock tank 38 is heated to about 180° C. by the heating apparatus 31 and the $Ru(Cp)_2$ complex stored in the tank 38 is gradually sublimated. A carrier gas is introduced into the feedstock tank 38 through the inlet pipe 41 and the $Ru(Cp)_2$ complex sublimated in the feedstock tank 38 is transferred to the film forming chamber 30 through the feed pipe 42. Examples of the carrier gas include argon, helium and nitrogen gases. An oxygen gas is fed into the film forming chamber 30 through the oxygen gas inlet pipe 49. In the film forming chamber 30, vapor of the $Ru(Cp)_2$ complex is thermally decomposed together with oxygen and Ru or $RuO_2$ thus formed is deposited on a substrate 33. Consequently, a uniform ruthenium-containing thin film is formed.

EXAMPLES

Examples of this embodiment will be described in detail, together with Comparative Examples.

Example 2-1

First, a crude product of a $Ru(Cp)_2$ complex was obtained by using a ruthenium chloride and Cp. Then, the resulting crude product was sublimated to obtain a purified product. Then, 10 g of the purified product was dissolved in 50 ml of THF and the solution was filtered. The filtrate obtained by filtration was cooled to −20° C. and recrystallized to produce a $Ru(Cp)_2$ complex.

Example 2-2

In the same manner as in Example 2-1, except that the amount of THF was changed to 100 ml, a $Ru(Cp)_2$ complex was produced.

Example 2-3

In the same manner as in Example 2-1, except that the amount of THF was changed to 200 ml, a $Ru(Cp)_2$ complex was produced.

Comparative Example 2-1

In the same manner as in Example 2-1, except that n-pentane was used as the solvent and 1 g of the purified product was dissolved in 50 ml of n-pentane, a $Ru(Cp)_2$ complex was produced.

Comparative Example 2-2

In the same manner as in Comparative Example 2-1, except that the amount of n-pentane was changed to 100 ml, a $Ru(Cp)_2$ complex was produced.

Comparative Example 2-3

In the same manner as in Comparative Example 2-1, except that the amount of n-pentane was changed to 200 ml, a $Ru(Cp)_2$ complex was produced.

Comparative Example 2-4

In the same manner as in Comparative Example 2-1, except that recrystallization was not performed, a $Ru(Cp)_2$ complex was produced.

Comparative Evaluation 2-1

The content of Ca in the Ru(Cp)$_2$ complexes obtained in Examples 2-1 to 2-3 and Comparative Examples 2-1 to 2-4 was measured. The results are shown in Table 3.

TABLE 3

| | Solvent | Amount of solvent (ml) | Ca content (ppm) |
|---|---|---|---|
| Example 2-1 | THF | 50 | 3.2 |
| Example 2-2 | THF | 100 | 0.7 |
| Example 2-3 | THF | 200 | <0.1 |
| Comparative Example 2-1 | n-pentane | 50 | 8.6 |
| Comparative Example 2-2 | n-pentane | 100 | 7.2 |
| Comparative Example 2-3 | n-pentane | 200 | 6.0 |
| Comparative Example 2-4 | — | 0 | 18.0 |

As is apparent from Table 3, the content of Ca of the Ru(Cp)$_2$ of Comparative Examples 2 to 4 obtained without subjecting to the recrystallization step was 18.0 ppm and the content of calcium considerably varies depending on the presence or absence of the recrystallization step. The Ca content of the Ru(Cp)$_2$ complexes of Examples 2-1 to 2-3 obtained by using THF as the solvent drastically decreases as compared with the Ru(Cp)$_2$ complexes of Comparative Examples 2-1 to 2-3 obtained by using n-pentane which has conventionally been used as the solvent. Comparing the Ru(Cp)$_2$ complexes of Examples 2-1 to 2-3, the Ca content tends to decrease as the amount of the solvent THF increases.

Example 2-4

A Ru(Cp)$_2$ complex having a calcium content of 0.1 ppm or less was sealed in an ampule bottle under an argon atmosphere. The ampule bottle was heated to 200° C. by a heating furnace and then maintained at the same temperature for 72 hours. The ampule bottle was taken out from the heating furnace and air-cooled to room temperature. The MS spectrum of the ruthenium compound cooled to room temperature in the ampule bottle was measured by a DI-MS apparatus (manufactured by JEOL, Ltd.). The measuring conditions by the DI-MS apparatus are shown in Table 4.

TABLE 4

| | |
|---|---|
| Ionization temperature | 180° C. |
| Ionization pressure | 5 × 10$^{-5}$ Pa |
| Ionization voltage | 20 V |
| Ionization current | 100 μA |
| Measuring apparatus | JMS-505HA, manufactured by JEOL, Ltd. |

Example 2-5

In the same manner as in Example 2-4, except for using a Ru(Cp)$_2$ complex having a calcium content of 0.7 ppm, the MS spectrum was measured by the DI-MS apparatus.

Example 2-6

In the same manner as in Example 2-4, except for using a Ru(Cp)$_2$ complex having a calcium content of 3.2 ppm, the MS spectrum was measured by the TG-DTA apparatus.

Comparative Example 2-5

In the same manner as in Example 2-4, except for using a Ru(Cp)$_2$ complex having a calcium content of 6.0 ppm, the MS spectrum was measured by the TG-DTA apparatus.

Comparative Evaluation 2-2

A fragment ratio determined from the results of the MS spectrum obtained in Examples 2-4 to 2-6 and Comparative Example 2-5 are shown in Table 5. The fragment ratio was determined by the following equation.

$$\text{(Fragment ratio)} = \{(\text{Fragment intensity of } [\text{Ru(Cp)}]^+)/ (\text{Fragment intensity of } [\text{Ru(Cp)}_2]^+)\} \times 100 \quad (7)$$

In the above equation (7), a large fragment ratio means that the amount of [Ru(Cp)]$^+$ is larger than that of [Ru(Cp)$_2$]$^+$ and also means a weak binding energy between Ru and Cp.

TABLE 5

| | Ca content (ppm) | Fragment ratio |
|---|---|---|
| Example 2-4 | <0.1 | 5.7 |
| Example 2-5 | 0.7 | 6.3 |
| Example 2-6 | 3.2 | 6.9 |
| Comparative Example 2-5 | 6.0 | 8.8 |

As is apparent from Table 5, in Comparative Example 2-5 wherein the content of impurities in the Ru(Cp)$_2$ complex exceeds 5 ppm exhibits a large fragment ratio even if the ionization voltage is controlled to the same ionization voltage after storage at a temperature higher than that of Examples 2-4 to 2-6, and thus resulting in a weak binding energy between Ru and Cp. In the MOCVD method, it can be assumed that weak binding energy between Ru and Cp makes the feed amount of the Ru(Cp)$_2$ as the feedstock unstable, and thus making the film forming rate unstable. On the other hand, Examples 2-4 to 2-6 wherein the content of impurities in the Ru(Cp)$_2$ complex is controlled within the range defined in the present invention exhibits a small fragment ratio, thus resulting in a weak binding energy between Ru and Cp. Herefrom, in the case of a small Ca content, because of less decomposition product of Ca(Cp)$_2$ and less degree of alteration of the Ru(Cp)$_2$ complex caused by the composite, the decrease of the binding energy between Ru and Cp of Ru(Cp)$_2$ and the deterioration of vaporization characteristics of the Ru(Cp)$_2$ complex are suppressed.

THIRD EMBODIMENT

The present inventors have intensively researched on an influence of impurities contained in a ruthenium compound on the film formation using the MOCVD method and confirmed that characteristics of the ruthenium compound can be improved by optimizing the content of either or both of iron and nickel among impurities contained in the ruthenium compound.

The ruthenium compound of the present invention is a ruthenium compound comprising a Ru(Cp)$_2$ complex, wherein the content of either or both of iron and nickel in the compound is 5 ppm or less. When the content of impurities exceeds 5 ppm, characteristics of the Ru(Cp)$_2$ complex deteriorate. The content of impurities is preferably from 0 to 5 ppm, more preferably from 0 to 2 ppm, and still more preferably from 0 to 0.1 ppm.

The method of producing a ruthenium compound of the present invention will now be described.

Figure 5:
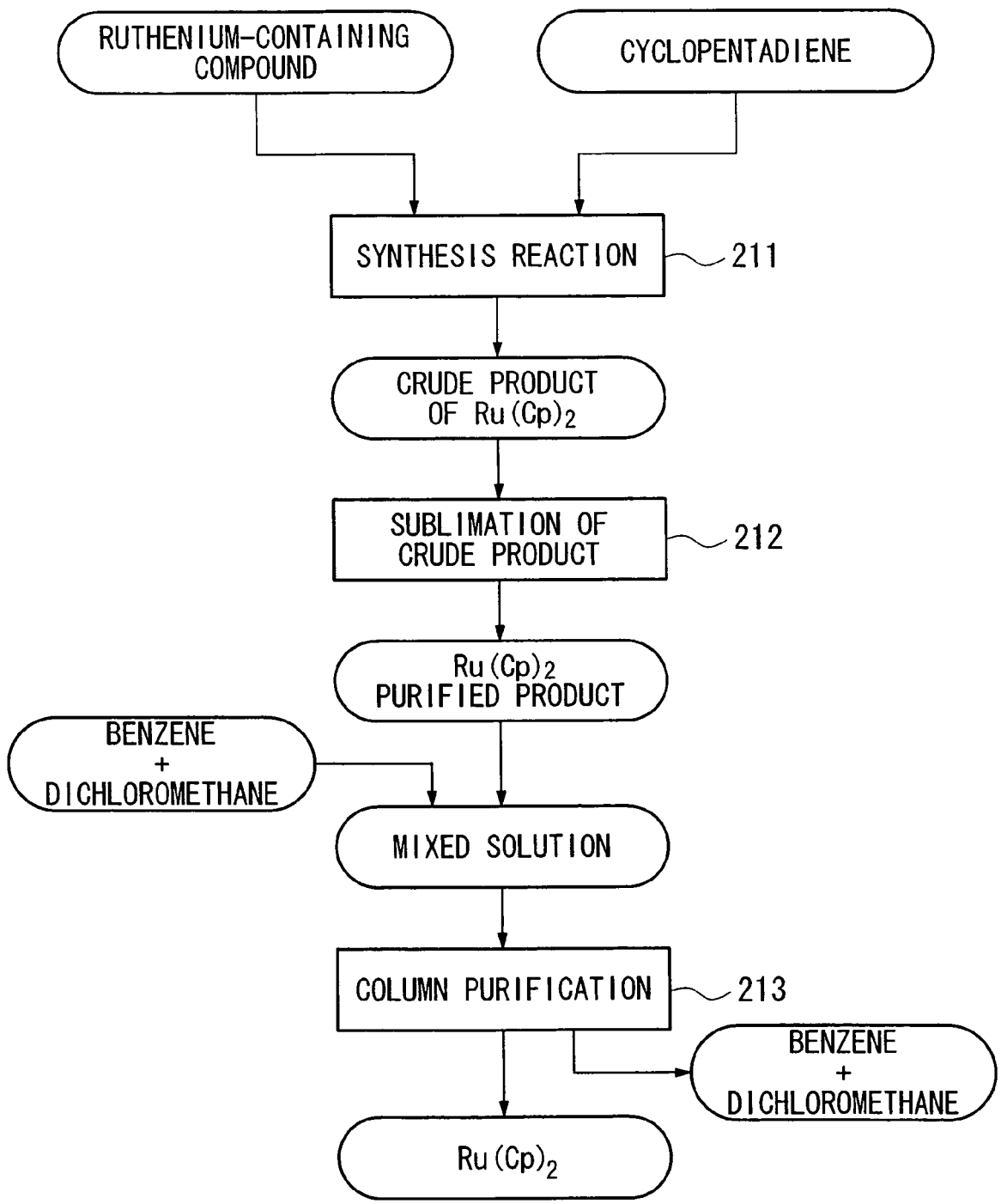
FIG. 5 is a flow chart showing the respective steps of a method of producing a ruthenium compound according to the third embodiment of the present invention.

First, as shown in FIG. 5, a crude product of a $Ru(Cp)_2$ complex is obtained by using a ruthenium-containing compound and Cp (step 211). In this step 211, a crude product of a $Ru(Cp)_2$ complex is obtained by a synthesis method which has conventionally been performed.

In the first solvent, ruthenium chloride hydrate $RuCl_3 \cdot nH_2O$ is dissolved. Examples of the first solvent include alcohols such as ethanol, isopropanol, and methanol. The reaction shown in the following scheme (8) is performed by adding Cp to the solution and further adding a metallic zinc powder.

$$2RuCl_3 + 4C_5H_6 + 3Zn \rightarrow 2Ru(Cp)_2 + 3ZnCl_2 + 2H_2 \qquad (8)$$

After filtering the reaction solution to remove the first solvent and zinc chloride dissolved in the solvent, the reaction product collected by filtration is extracted by dissolving in the second solvent. Examples of the second solvent include tetrahydrofuran, benzene, and n-pentane. A crude product of a $Ru(Cp)_2$ complex is obtained by removing the second solvent from the extract.

A crude product of a $Ru(Cp)_2$ complex may also be synthesized by using the method described in Organic synthesis, pp. 96–98 (1961). According to the method described in the above document, sodium is suspended in 1,2-dimethoxyethane and Cp is added dropwise in the suspension, thereby to dissolve sodium. In this case, the reaction shown in the following scheme (9) arises.

$$2C_5H_6 + 2Na \rightarrow 2C_5H_5^- Na^+ + H_2 \qquad (9)$$

When evolution of hydrogen is completed by the reaction between Cp and sodium, the mixed solution is maintained at a temperature which is slightly lower than the reflux temperature. When the entire sodium is not dissolved, the solution is cooled to room temperature and several ml of Cp is added, and then the mixed solution is heated again until sodium is completely dissolved. After the completion of the reaction shown in the scheme (9), ruthenium trichloride and metallic ruthenium are added to the mixed solution and, after maintaining at the temperature which is slightly lower than the reflux temperature, the mixture is reacted by heating with stirring under a nitrogen atmosphere. In this case, the reaction is shown in the following scheme (10).

$$6C_5H_5^- Na^+ + 2RuCl_3 + Ru \rightarrow 3Ru(Cp)_2 + 6NaCl \qquad (10)$$

After the completion of the reaction shown in the scheme (10), the solvent is removed while stirring using an aspirator to obtain a crude product of a $Ru(Cp)_2$ complex.

While the above two kinds of synthesis reactions were described as the reaction for obtaining the crude product of the step 211 in this embodiment, the reaction is not limited to these synthesis reactions.

Next, the resulting crude product is sublimated to obtain a purified product (step 212).

In this step 212, the crude product is sublimated by evacuation or heating, and then the sublimate is collected and purified.

Next, the purified product is dissolved in a solvent and the solution is repurified by passing through an alumina column (step 213).

The method of the present invention is characterized in that a mixed solvent obtained by adding 10 to 30 mol % of dichloromethane to 90 to 70 mol % of benzene is used as an eluent. By using an eluent having a controlled polarity suited to remove iron or nickel obtained by adding 10 to 30 mol % of dichloromethane as a polar solvent to 90 to 70 mol % of benzene as a non-polar solvent in the column purification step, the amount of iron or nickel as impurities after recrystallization can be considerably decreased. A mixed solvent obtained by adding 15 to 25 mol % of dichloromethane to 90 to 70 mol % of benzene is preferable. When the amount of dichloromethane to be added is less than 10 mol % or exceed 30 mol %, there arises a problem that the content of Fe and Ni increases.

As described above, by passing through the steps 211 and 213, it is made possible to obtain a $Ru(Cp)_2$ complex wherein the content of either or both of iron and nickel is 5 ppm or less, which is a ruthenium compound of the present invention.

The constitution of the MOCVD apparatus that employs a solid sublimation method of this embodiment is almost the same as that of the apparatus described with reference to FIG. 3 in the first embodiment, and the apparatus comprises a film forming chamber 30, the entire apparatus being covered with a heating apparatus 31. In the film forming chamber 30, a heater 32 is provided and a substrate 33 is held on the heater 32. The film forming chamber 30 is evacuated through a piping 37 equipped with a pressure gauge 34 and a needle valve 36. The heating apparatus 31 is provided with a feedstock tank 38 and, in this embodiment, a $Ru(Cp)_2$ complex which is solid at normal temperature, the content of either or both of iron and nickel being controlled to 5 ppm or less, is stored in the feedstock tank 38. A carrier gas inlet pipe 41 is connected to the feedstock tank 38 via a gas flow controller 39, and a feed pipe 42 is connected to the feedstock tank 38. The feed pipe 42 is provided with a filter 43, a needle valve 44 and a gas flow controller 46, and the feed pipe 42 is connected to the film forming chamber 30. To the film forming chamber 30, an oxygen gas inlet pipe 49 is connected via a needle valve 47 and a gas flow controller 48.

In this apparatus, the feedstock tank 38 is heated to about 180° C. by the heating apparatus 31 and the $Ru(Cp)_2$ complex stored in the tank 38 is gradually sublimated. A carrier gas is introduced into the feedstock tank 38 through the inlet pipe 41 and the $Ru(Cp)_2$ complex sublimated in the feedstock tank 38 is transferred to the film forming chamber 30 through the feed pipe 42. Examples of the carrier gas include argon, helium and nitrogen gases. An oxygen gas is fed into the film forming chamber 30 through the oxygen gas inlet pipe 49. In the film forming chamber 30, vapor of the $Ru(Cp)_2$ complex is thermally decomposed together with oxygen and Ru or $RuO_2$ thus formed is deposited on a substrate 33. Consequently, a uniform ruthenium-containing thin film is formed.

EXAMPLES

Examples of this embodiment will be described in detail, together with Comparative Examples.

Example 3-1

As an eluent for the column purification step, a solvent such as benzene, and three kinds of mixed solvents prepared by adding 10 mol %, 20 mol % and 30 mol % of dichloromethane to 90 mol %, 80 mol % and 70 mol % of benzene were used.

First, a crude product of a $Ru(Cp)_2$ complex was obtained by using a ruthenium chloride and Cp. Then, the resulting crude product was sublimated to obtain a purified product. After dividing the purified product into four portions, each portion of the purified product was dissolved in four kinds of eluents and the solution was passed through a column. Then, the eluents were removed to produce $Ru(Cp)_2$ complexes. The content of Fe and Ni in the resulting $Ru(Cp)_2$ complexes was measured. The results are shown in Table 6

TABLE 6

| Amount of dichloromethane added in eluent (mol %) | Fe content (ppm) | Ni content (ppm) |
| --- | --- | --- |
| 0 | 5.8 | 6.4 |
| 10 | 2.9 | 3.6 |
| 20 | <0.1 | <0.1 |
| 30 | 1.2 | 1.2 |

As is apparent from Table 6, in the $Ru(Cp)_2$ complexes produced by using mixed solvents prepared by adding 10 mol %, 20 mol % and 30 mol % of dichloromethane based on 100% of benzene as the eluent, Fe and Ni contents decreased as compared with the $Ru(Cp)_2$ complex produced by using benzene which has conventionally been used. Examining the relation between the amount of dichloromethane to be added and Fe and Ni contents, Fe and Ni contents in the $Ru(Cp)_2$ complex decrease when the amount of dichloromethane to be added is 20 mol %.

Example 3-2

A $Ru(Cp)_2$ complex having an iron content of 0.1 ppm or less was sealed in an ampule bottle under an argon atmosphere. The ampule bottle was heated to 200° C. by a heating furnace and then maintained at the same temperature for 72 hours. The ampule bottle was taken out from the heating furnace and air-cooled to room temperature. The vaporization rate of the ruthenium compound cooled to room temperature in the ampule bottle was measured by using a TG-DTA apparatus (manufactured by MAC-Science Co.). The measuring conditions by the TG-DTA apparatus are shown in Table 7.

TABLE 7

| | |
| --- | --- |
| Temperature | 135° C. |
| Pressure | 101.3 kPa |
| Carrier gas (Ar) flow rate | 100 sccm |
| Measuring cell | made of alumina |
| Measuring apparatus | TGA-2000, manufactured by MAC-Science Co. |

Example 3-3

In the same manner as in Example 3-2, except for using a $Ru(Cp)_2$ complex having an iron content of 1.2 ppm, the vaporization rate was measured by the TG-DTA apparatus.

Example 3-4

In the same manner as in Example 3-2, except for using a $Ru(Cp)_2$ complex having an iron content of 2.9 ppm, the vaporization rate was measured by the TG-DTA apparatus.

Example 3-5

In the same manner as in Example 3-2, except for using a $Ru(Cp)_2$ complex having a nickel content of 0.1 ppm or less, the vaporization rate was measured by the TG-DTA apparatus.

Example 3-6

In the same manner as in Example 3-2, except for using a $Ru(Cp)_2$ complex having a nickel content of 1.2 ppm, the vaporization rate was measured by the TG-DTA apparatus.

Example 3-7

In the same manner as in Example 3-2, except for using a $Ru(Cp)_2$ complex having a nickel content of 3.6 ppm, the vaporization rate was measured by the TG-DTA apparatus.

Comparative Example 3-1

In the same manner as in Example 3-2, except for using a $Ru(Cp)_2$ complex having an iron content of 5.8 ppm, the vaporization rate was measured by the TG-DTA apparatus.

Comparative Example 3-2

In the same manner as in Example 3-2, except for using a $Ru(Cp)_2$ complex having a nickel content of 6.4 ppm, the vaporization rate was measured by the TG-DTA apparatus.

<Comparison Test and Evaluation>

The vaporization rate of the ruthenium compounds obtained in Examples 3-2 to 3-7 and Comparative Examples 3-1 and 3-2 was measured by a TG-DTA apparatus. The results are shown in Table 8.

TABLE 8

| | Impurities and content (ppm) | | Vaporization rate (μg/min) |
| --- | --- | --- | --- |
| Example 3-2 | Fe | <0.1 | 142 |
| Example 3-3 | Fe | 1.2 | 138 |
| Example 3-4 | Fe | 2.9 | 127 |
| Example 3-5 | Ni | <0.1 | 142 |
| Example 3-6 | Ni | 1.2 | 138 |
| Example 3-7 | Ni | 3.6 | 125 |
| Comparative Example 3-1 | Fe | 5.8 | 91 |
| Comparative Example 3-2 | Ni | 6.4 | 94 |

As is apparent from Table 8, Comparative Examples 3-1 and 3-2 wherein the content of iron and nickel as impurities in the $Ru(Cp)_2$ complex exceeds 5 ppm were inferior in vaporization rate to Examples 3-2 to 3-7. As a result, it has been found that vaporization characteristics of the $Ru(Cp)_2$ complex containing impurities such as iron and nickel in an amount greater than the range defined in the present invention deteriorate after storage at high temperature. This means that the film forming rate decreases because the feed amount of the $Ru(Cp)_2$ complex as the feedstock decreases by the reduction of the vaporization rate in the case of forming a film by the MOCVD method. On the other hand, in Examples 3-2 to 3-7 wherein the amount of impurities such as iron and nickel in the $Ru(Cp)_2$ complex is controlled within the range defined in the present invention, the vaporization rate is higher than that of Comparative Examples 3-1 and 3-2. The reason is believed to be as follows. That is, deterioration of vaporization characteristics of the $Ru(Cp)_2$ complex was suppressed because of less composite made of iron or nickel and Cp and less degree of alteration of the $Ru(Cp)_2$ complex caused by the composite.

FOURTH EMBODIMENT

The present inventors have intensively researched on an influence of impurities contained in a ruthenium compound on the film formation using the MOCVD method and confirmed that characteristics of the ruthenium compound can be improved by optimizing the content of zinc among impurities contained in the ruthenium compound.

The ruthenium compound of the present invention is a ruthenium compound comprising a Ru(Cp)$_2$ complex, wherein the content of zinc in the compound is 5 ppm or less. When the content of impurities exceeds 5 ppm, characteristics of the Ru(Cp)$_2$ complex deteriorate. The content of impurities is preferably from 0 to 5 ppm, more preferably from 0 to 4 ppm, and still more preferably from 0 to 0.1 ppm.

The method of producing a ruthenium compound of the present invention will now be described.

Figure 6:
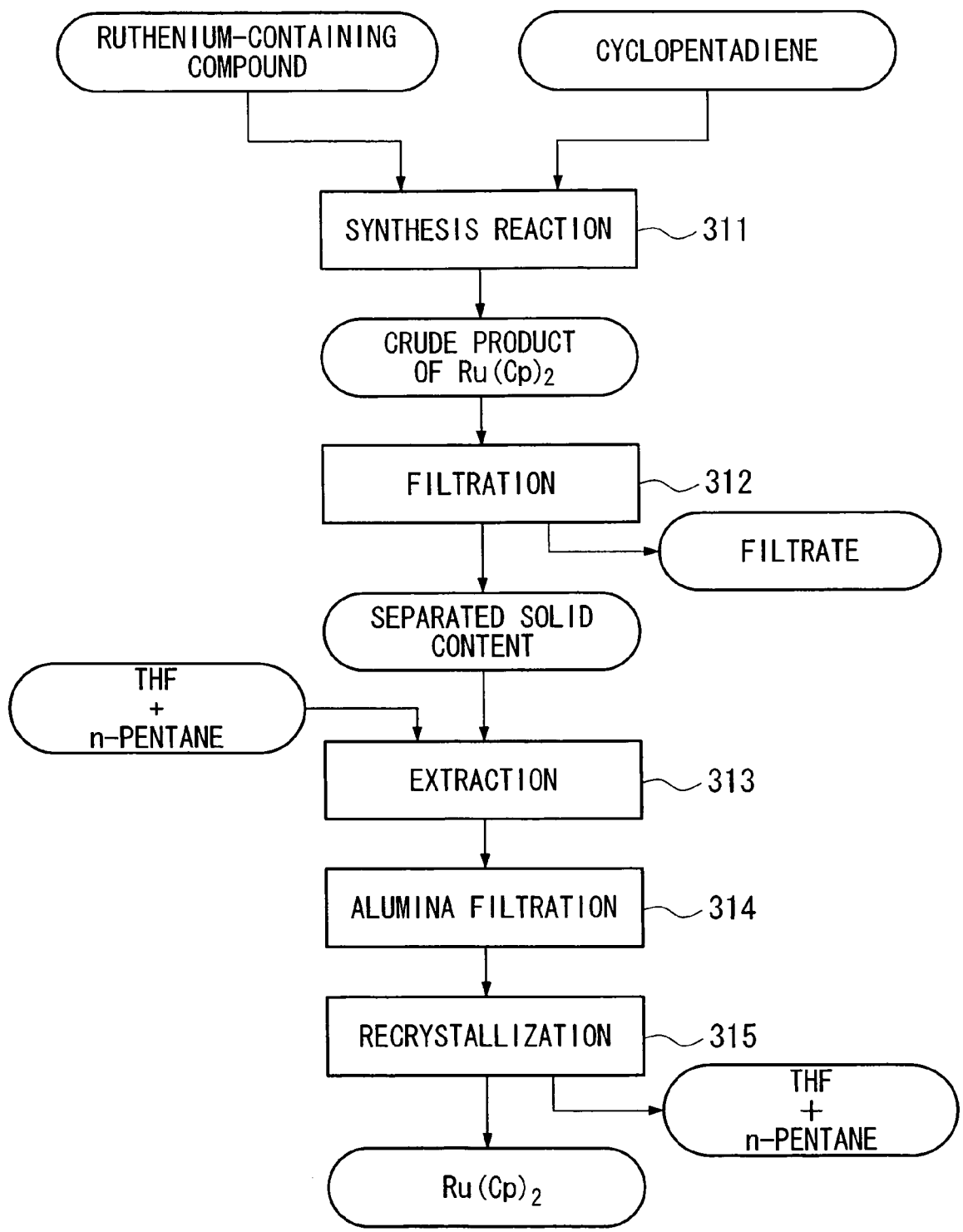
FIG. 6 is a flow chart showing the respective steps of a method of producing a ruthenium compound according to the fourth embodiment of the present invention.

First, as shown in FIG. 6, a crude product of a Ru(Cp)$_2$ complex is obtained by using a ruthenium-containing compound and Cp (step 311). In this step 311, a crude product is obtained by a synthesis method which has conventionally been performed.

In the first solvent, ruthenium chloride hydrate RuCl$_3$.nH$_2$O is dissolved. Examples of the first solvent include alcohols such as ethanol, isopropanol, and methanol. The reaction shown in the following scheme (11) is performed by adding Cp to the solution and further adding a metallic zinc powder.

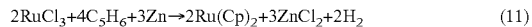

$$2RuCl_3 + 4C_5H_6 + 3Zn \rightarrow 2Ru(Cp)_2 + 3ZnCl_2 + 2H_2 \quad (11)$$

After filtering the reaction solution to remove the first solvent and zinc chloride dissolved in the solvent, the reaction product collected by filtration is extracted by dissolving in the second solvent. Examples of the second solvent include tetrahydrofuran, benzene, and n-pentane. A crude product of a Ru(Cp)$_2$ complex is obtained by removing the second solvent from the extract.

While the above synthesis reaction was described as the reaction for obtaining the crude product of the step 311 in this embodiment, the reaction is not limited to this synthesis reaction.

Next, a solution containing the resulting crude product is filtered (step 312).

In this step 312, the reaction solvent used in the case of synthesizing the crude product is removed.

Next, the crude product collected by filtration is extracted (step 313).

The method of the present invention is characterized in that the solvent used in the extraction step 313 is a mixed solvent containing THF and n-pentane and a weight ratio of THF to n-pentane in the mixed solvent (THF/n-pentane) is controlled within a range from 5/5 to 2/8. By using the mixed solvent wherein the weight ratio of THF to n-pentane is within the above range as the eluent, a zinc compound contained in the crude product collected by filtration can be highly dissolved as compared with the case of using a conventional eluent. When the mixing ratio is less than 5/5, since zinc chloride contained in the crude product is dissolved in THF, sufficient purification cannot be performed. On the other hand, when the mixing ratio exceeds 2/8, there arises a problem that an organic complex compound of zinc is not sufficiently dissolved in the solvent. The weight ratio is preferably from 5/5 to 2/8, and more preferably from 3/7 to 2/8.

Next, the solution containing the extracted crude product is purified by passing through an alumina column (step 314).

By passing through the alumina column, inorganic and organic impurities in the extract are removed. Because of proper polarity between an alumina, which is a filler of the alumina column, and the solvent used in the above-described extraction step 313, the amount of zinc as impurities after passing through the alumina column can be considerably decreased.

The solution containing the crude product is recrystallized (step 315).

The eluent is removed by recrystallization to obtain a purified product of a Ru(Cp)$_2$ complex.

As described above, by passing through the steps 311 to 315, it is made possible to obtain a Ru(Cp)$_2$ complex wherein the content of zinc is 5 ppm or less, which is a ruthenium compound of the present invention.

The constitution of the MOCVD apparatus that employs a solid sublimation method of this embodiment is almost the same as that of the apparatus described with reference to FIG. 3 in the first embodiment, and the apparatus comprises a film forming chamber 30, the entire apparatus being covered with a heating apparatus 31. In the film forming chamber 30, a heater 32 is provided and a substrate 33 is held on the heater 32. The film forming chamber 30 is evacuated through a piping 37 equipped with a pressure gauge 34 and a needle valve 36. The heating apparatus 31 is provided with a feedstock tank 38 and, in this embodiment, a Ru(Cp)$_2$ complex which is solid at normal temperature, the content of zinc being controlled to 5 ppm or less, is stored in the feedstock tank 38. A carrier gas inlet pipe 41 is connected to the feedstock tank 38 via a gas flow controller 39, and a feed pipe 42 is connected to the feedstock tank 38. The feed pipe 42 is provided with a filter 43, a needle valve 44 and a gas flow controller 46, and the feed pipe 42 is connected to the film forming chamber 30. To the film forming chamber 30, an oxygen gas inlet pipe 49 is connected via a needle valve 47 and a gas flow controller 48.

In this apparatus, the feedstock tank 38 is heated to about 180° C. by the heating apparatus 31 and the Ru(Cp)$_2$ complex stored in the tank 38 is gradually sublimated. A carrier gas is introduced into the feedstock tank 38 through the inlet pipe 41 and the Ru(Cp)$_2$ complex sublimated in the feedstock tank 38 is transferred to the film forming chamber 30 through the feed pipe 42. Examples of the carrier gas include argon, helium and nitrogen gases. An oxygen gas is fed into the film forming chamber 30 through the oxygen gas inlet pipe 49. In the film forming chamber 30, vapor of the Ru(Cp)$_2$ complex is thermally decomposed together with oxygen and Ru or RuO$_2$ thus formed is deposited on a substrate 33. Consequently, a uniform ruthenium-containing thin film is formed.

EXAMPLES

Examples of this embodiment will be described in detail, together with Comparative Examples.

Example 4-1

A solvent composed only of THF, mixed solvents prepared by mixing THF and n-pentane in a weight ratio (THF/n-pentane) of 7/3, 5/5, 3/7 and 2/8, and a solvent composed of n-pentane were used as the eluent.

First, a crude product of a Ru(Cp)$_2$ complex was obtained by using a ruthenium chloride and Cp. Then, a solution containing the resulting crude product was filtered by passing through a filter. After dividing the crude product collected by filtration into six portions, each portion of the crude product was added to six kinds of eluents to obtain extracts. Then, the extracts containing the extracted crude product were purified while passing through an alumina column, and then the extracts containing the extracted crude product were recrystallized to produce $Ru(Cp)_2$ complexes. The content of Zn in the resulting $Ru(Cp)_2$ complexes was measured. The results are shown in Table 9.

TABLE 9

| Mixing ratio of solvent | | Zn content |
|---|---|---|
| THF | n-pentane | (ppm) |
| 1 | 0 | 8.7 |
| 7 | 3 | 5.8 |
| 5 | 5 | 4.0 |
| 3 | 7 | <0.1 |
| 2 | 8 | 3.1 |
| 0 | 1 | 6.3 |

As is apparent from Table 9, the $Ru(Cp)_2$ complexes produced by using a solvent composed of only THF and a solvent composed of only n-pentane as the eluent had a large Zn content. In the $Ru(Cp)_2$ complexes produced by using mixed solvents of THF and n-pentane As the eluent, when using the mixed solvent prepared by mixing THF and n-pentane In a weight ratio (THF/n-pentane) of 7/3 as the eluent, the content of Zn was not Within the range defined in the present invention. It has been found that the Zn content in The $Ru(Cp)_2$ complex is decreased in the case of the $Ru(Cp)_2$ complex obtained by using The mixed solvent prepared by mixing THF and n-pentane in a weight ratio 3/7 as the Eluent among the $Ru(Cp)_2$ complexes obtained by using the mixed solvent prepared by Mixing THF and n-pentane in a weight ratio of 5/5, 3/7 and 2/8.

Example 4-2a

A $Ru(Cp)_2$ complex having a zinc content of 0.1 ppm or less was sealed in an ampule bottle under an argon atmosphere. The ampule bottle was heated to 200° C. by a heating furnace and then maintained at the same temperature for 72 hours. The ampule bottle was taken out from the heating furnace and air-cooled to room temperature. The vaporization ratio of the ruthenium compound cooled to room temperature in the ampule bottle were measured by using a TG-DTA apparatus (manufactured by MAC-Science Co.). The measuring conditions by the TG-DTA apparatus are shown in Table 10.

TABLE 10

| Temperature | 25° C.–500° C. |
|---|---|
| | (Heating rate: 10° C./min) |
| Pressure | 101.3 kPa |
| Carrier gas (Ar) flow rate | 100 sccm |
| Measuring cell | made of alumina |
| Measuring apparatus | TGA-2000, manufactured by MAC-Science Co. |

Example 4-2b

In the same manner as in Example 4-1, except for using a $Ru(Cp)_2$ complex having a zinc content of 3.1 ppm, the vaporization ratio was measured by the TG-DTA apparatus.

Example 4-3

In the same manner as in Example 4-1, except for using a $Ru(Cp)_2$ complex having a zinc content of 4.0 ppm, the vaporization ratio was measured by the TG-DTA apparatus.

Comparative Example 4-1

In the same manner as in Example 4-1, except for using a $Ru(Cp)_2$ complex having a zinc content of 5.8 ppm, the vaporization ratio was measured by the TG-DTA apparatus.

<Comparison Test and Evaluation>

The vaporization ratio of the ruthenium compounds obtained in Examples 4-2a, 4-2b and 4-3 and Comparative Example 4-1 was measured by a TG-DTA apparatus. The results are shown in Table 11.

TABLE 11

| | Zn content (ppm) | Vaporization ratio (% by weight) |
|---|---|---|
| Example 4-2a | <0.1 | 100 |
| Example 4-2b | 3.1 | 100 |
| Example 4-3 | 4.0 | 99 |
| Comparative Example 4-1 | 5.8 | 94 |

As is apparent from Table 11, in Comparative Example 4-1 wherein the content of impurities in the $Ru(Cp)_2$ complex exceeds 5 ppm, decrease in vaporization ratio increased as compared with Examples 4-2a, 4-2b and 4-3. As a result, it has been found that vaporization characteristics of the $Ru(Cp)_2$ complexes containing impurities in the amount greater than the range defined in the present invention deteriorate after storage at high temperature. In Examples 4-2a, 4-2b and 4-3 wherein the content of zinc in the $Ru(Cp)_2$ complex is controlled within the range defined in the present invention, the vaporization ratio slightly increased. The reason is believed to be as follows. That is, vaporization characteristics of the $Ru(Cp)_2$ complex slightly deteriorated because of less decomposition product of a zinc compound, less separation of Cp or chlorine, and less degree of alteration of the $Ru(Cp)_2$ complex.

FIFTH EMBODIMENT

The present inventors have intensively researched on an influence of impurities contained in a ruthenium compound on the film formation using the MOCVD method and confirmed that characteristics of the ruthenium compound can be improved by optimizing the content of rhenium among impurities contained in the ruthenium compound.

The ruthenium compound of the present invention is a ruthenium compound comprising a $Ru(Cp)_2$ complex, wherein the content of rhenium in the compound is from 10 to 100 ppm. When a film is formed on a substrate by using a ruthenium compound containing rhenium in the amount controlled to the specific numerical value within the above range as a feedstock for MOCVD, first, a rhenium compound, which is easily decomposed as compared with the ruthenium compound, is decomposed and deposited on the substrate as a nucleus for the growth of the film. Then, the ruthenium compound grows in the presence of this nucleus as a center to form a thin film. Therefore, since the nucleus made of a given amount of rhenium is always formed on the substrate upon formation of a ruthenium-containing thin film by forming a film on the substrate using the ruthenium compound containing rhenium in the amount controlled to the specific numerical value within the above range as the feedstock, a proper film forming rate can be obtained.

The ruthenium compound of the present invention contains rhenium in the amount of 10 to 100 ppm. The content is preferably from 10 to 85 ppm, more preferably from 19 to 68 ppm, and still more preferably from 19 to 42 ppm. When the rhenium content is less than 10 ppm, a nucleus made of rhenium required to form the ruthenium-containing thin film is not sufficiently formed, and thus a proper film forming rate can be obtained. On the other hand, when the rhenium content exceeds 100 ppm, the rhenium compound is excessively decomposed, and thus the rhenium decomposed product and the $Ru(Cp)_2$ complex form a hardly vaporizable composite, thereby lowering the vaporization rate.

The method of producing a ruthenium compound for MOCVD method of the present invention will now be described.

First, ruthenium chloride hydrate $RuCl_3.nH_2O$ and rhenium chloride $ReCl_3$ are dissolved in the first solvent. Examples of the first solvent include alcohols such as ethanol, isopropanol, and methanol. The amount of rhenium chloride is adjusted so that the rhenium content in the resulting ruthenium compound is from 10 to 100 ppm. Then, the reaction is performed by adding cyclopentadiene to the solution and further adding a metallic zinc powder. After filtering the reaction solution to remove the first solvent, the reaction product is dissolved in the second solvent and extracted. Examples of the second solvent include tetrahydrofuran and benzene. Furthermore, a $Ru(Cp)_2$ complex containing 10 to 100 ppm of rhenium, which is a ruthenium compound of the present invention, is obtained by removing the second solvent from the extract and sublimating under reduced pressure.

The constitution of the MOCVD apparatus that employs a solid sublimation method of this embodiment is almost the same as that of the apparatus described with reference to FIG. 3 in the first embodiment, and the apparatus comprises a film forming chamber 30, the entire apparatus being covered with a heating apparatus 31. In the film forming chamber 30, a heater 32 is provided and a substrate 33 is held on the heater 32. The film forming chamber 30 is evacuated through a piping 37 equipped with a pressure gauge 34 and a needle valve 36. The heating apparatus 31 is provided with a feedstock tank 38 and, in this embodiment, a $Ru(Cp)_2$ complex, which is solid at normal temperature and contains 10 to 100 ppm of rhenium, is stored in the feedstock tank 38. A carrier gas inlet pipe 41 is connected to the feedstock tank 38 via a gas flow controller 39, and a feed pipe 42 is connected to the feedstock tank 38. The feed pipe 42 is provided with a filter 43, a needle valve 44 and a gas flow controller 46, and the feed pipe 42 is connected to the film forming chamber 30. To the film forming chamber 30, an oxygen gas inlet pipe 49 is connected via a needle valve 47 and a gas flow controller 48.

In this apparatus, the feedstock tank 38 is heated to about 180° C. by the heating apparatus 31 and the $Ru(Cp)_2$ complex stored in the tank 38 is gradually sublimated. A carrier gas is introduced into the feedstock tank 38 through the inlet pipe 41 and the $Ru(Cp)_2$ complex sublimated in the feedstock tank 38 is transferred to the film forming chamber 30 through the feed pipe 42. Examples of the carrier gas include argon, helium and nitrogen gases. An oxygen gas is fed into the film forming chamber 30 through the oxygen gas inlet pipe 49. In the film forming chamber 30, first, the rhenium compound, which is easily decomposed as compared with the $Ru(Cp)_2$ complex, is decomposed and deposited as a nucleus for the growth of the film on a heated substrate. Then, vapor of the $Ru(Cp)_2$ complex is thermally decomposed together with oxygen and Ru or $RuO_2$ thus formed is deposited on a substrate 33. Consequently, a uniform ruthenium-containing thin film is formed.

EXAMPLES

Examples of this embodiment will be described in detail, together with Comparative Examples.

Example 5-1

First, a $Ru(Cp)_2$ complex containing 10 ppm of rhenium was prepared. Then, a ruthenium-containing thin film having a thickness of about 200 nm was formed on a substrate by feeding the complex as a feedstock on the substrate using a MOCVD apparatus shown in FIG. 3 that employs a solid sublimation method. The film forming conditions are as shown in Table 12.

TABLE 12

| | |
|---|---|
| Substrate temperature (° C.) | 450 |
| Pressure in film forming chamber (Pa) | 665 |
| Oxygen gas flow rate (sccm) | 50 |
| Carrier gas (Ar) flow rate (sccm) | 200 |
| Sublimation temperature (° C.) | 180 |

Example 5-2

Under the same conditions as in Example 5-1, except for using a $Ru(Cp)_2$ complex containing 19 ppm of rhenium, a ruthenium-containing thin film was formed on the substrate.

Example 5-3

Under the same conditions as in Example 5-1, except for using a $Ru(Cp)_2$ complex containing 42 ppm of rhenium, a ruthenium-containing thin film was formed on the substrate.

Example 5-4

Under the same conditions as in Example 5-1, except for using a $Ru(Cp)_2$ complex containing 68 ppm of rhenium, a ruthenium-containing thin film was formed on the substrate.

Example 5-5

Under the same conditions as in Example 5-1, except for using a $Ru(Cp)_2$ complex containing 85 ppm of rhenium, a ruthenium-containing thin film was formed on the substrate.

Comparative Example 5-1

Under the same conditions as in Example 5-1, except for using a $Ru(Cp)_2$ complex containing 7 ppm of rhenium, a ruthenium-containing thin film was formed on the substrate.

Comparative Example 5-2

Under the same conditions as in Example 5-1, except for using a $Ru(Cp)_2$ complex containing 103 ppm of rhenium, a ruthenium-containing thin film was formed on the substrate.

<Comparison Test 5-1>

The film forming rate of the ruthenium-containing thin films obtained in Examples 5-1 to 5-5 and Comparative Examples 5-1 to 5-2 was measured. The film forming rate of the resulting films is shown in FIG. 7.

Figure 7:
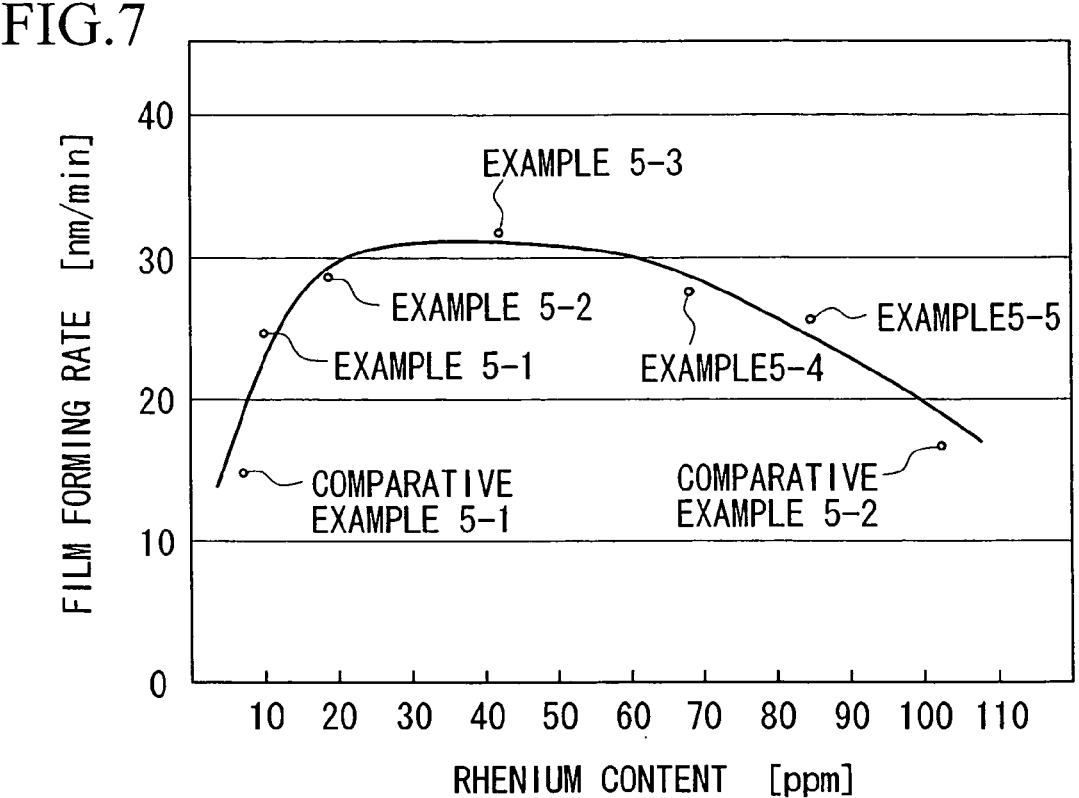
FIG. 7 is a graph showing the relationship between the rhenium content and the film forming rate.

As is apparent from FIG. 7, in Comparative Example 5-1 wherein a ruthenium compound having a small rhenium content, it is believed that the film forming rate decreased because there are few places capable of serving as a nucleus for the growth of the film. In Comparative Example 5-2 wherein a ruthenium compound has a large rhenium content, it is believed that the film forming rate decreased because the rhenium compound, which is easily decomposed as compared with the ruthenium compound, is excessively decomposed during storage at high temperature for vaporization, and thus a large amount of the rhenium decomposed product and the ruthenium compound form a hardly vaporizable composite. On the other hand, in Examples 5-1 to 5-5 wherein a ruthenium compound containing rhenium in the amount controlled to the numerical value within the above range defined in the present invention, a proper film forming rate can be obtained.

<Comparison Test 5-2>

The ruthenium compounds prepared in Examples 5-1 to 5-5 and Comparative Examples 5-1 to 5-2 were stored in heat under an argon atmosphere at 180° C. for one week. After the storage of the ruthenium compounds, the vaporization rate was measured under the following thermogravimetry conditions shown in Table 13 using a thermogravimetry apparatus (manufactured by MAC-Science Co.). The vaporization rate of the ruthenium compounds of Examples 5-1 to 5-5 and Comparatives Example 5-1 to 5-2 measured by thermogravimetry is shown in FIG. 8.

TABLE 13

| | |
|---|---|
| Temperature (° C.) | 135 |
| Pressure (kPa) | 101.3 |
| Carrier gas (Ar) flow rate (sccm) | 100 |
| Measuring cell | made of alumina |

Figure 8:
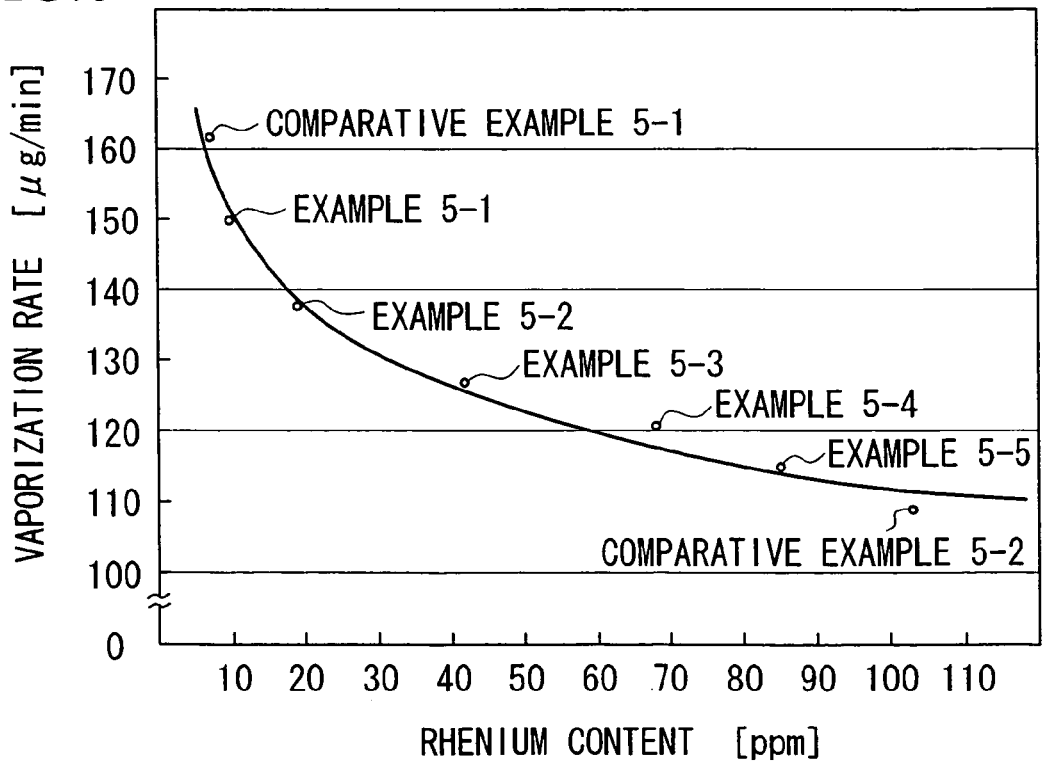
FIG. 8 is a graph showing the relationship between the rhenium content and the vaporization rate.

As is apparent from FIG. 8, the vaporization rate tends to decrease as the content of rhenium in the ruthenium compound increases. In Comparative Example 5-1, preferable results such as high vaporization rate were obtained. As is apparent from the results shown in FIG. 7, the film forming rate decreases because of less formation of a nucleus made of rhenium required for the growth of the film. In Comparative Example 5-2, it is believed that a composite comprising rhenium and a ruthenium compound was formed and a decrease in vaporization rate is caused by this composite. On the other hand, in Examples 5-1 to 5-5 wherein a ruthenium compound containing rhenium in the amount controlled to the numerical value within the above range defined in the present invention, a proper film forming rate can be obtained.

A ruthenium compound, which satisfies all conditions shown in the first embodiment to the fifth embodiment, may be employed. There may be employed a ruthenium compound wherein the content of either or both of sodium and potassium in the compound is 5 ppm or less, the content of calcium in the compound is 5 ppm or less, the content of either or both of iron and nickel in the compound is 5 ppm or less, the content of zinc in the compound is 5 ppm or less, and the content of rhenium in the compound is from 10 to 100 ppm. Furthermore, a ruthenium-containing thin film formed by using the ruthenium compound may be employed. Also in this case, the same effect as those of the first to fifth embodiments can be exerted, as a matter of course.

INDUSTRIAL APPLICABILITY

In the present invention, since the content of any one of sodium, potassium, calcium, Fe, Ni and Zn in a compound is adjusted to 5 ppm or less, deterioration of vaporization characteristics of a $Ru(Cp)_2$ complex can be suppressed. In the present invention, since the compound contains 10 to 100 ppm of rhenium, proper film forming rate can be obtained. Consequently, it is made possible to obtain a uniform ruthenium-containing thin film. Therefore, the resulting ruthenium-containing thin film is excellent in step coverage and surface morphology and is also excellent in electrical characteristics.

The invention claimed is:

1. A method for manufacturing a ruthenium compound, comprising:
    obtaining a crude product of a bis(cyclopentadienyl) ruthenium complex using a ruthenium-containing compound and cyclopentadiene,
    sublimating said resulting crude product and collecting a purified product;
    wherein a sublimate obtained by sublimation of said crude product is passed through a deposition inhibitor to remove either or both of sodium and potassium in the case of collecting said sublimate during said sublimation and collection.

2. A method for manufacturing a ruthenium compound, comprising:
    obtaining a crude product of a bis(cyclopentadienyl) ruthenium complex using a ruthenium-containing compound and cyclopentadiene,
    sublimating said resulting crude product to obtain a purified product,
    dissolving the purified product in tetrahydrofuran (THF) and filtering the resulting solution, and
    recrystallizing the purified product, from said solution,
    wherein the solvent used in said filtration is tetrahydrofuran (THF).

3. A method for manufacturing a ruthenium compound, comprising:
    obtaining a crude product of a bis(cyclopentadienyl) ruthenium complex using a ruthenium-containing compound and cyclopentadiene,
    sublimating said resulting crude product to obtain a purified product of said complex, and
    dissolving said purified product in a solvent and repurifying the dissolved solution by passing it through a column;
    wherein the eluent used in said column purification is a mixed solvent obtained by adding 10 to 30 mol % of dichloromethane to 90 to 70 mol % of benzene.

4. A method for manufacturing a ruthenium compound, comprising:
    obtaining a crude product of a bis(cyclopentadienyl) ruthenium complex using a ruthenium-containing compound and cyclopentadiene,
    filtering a solution containing said resulting crude product,
    extracting said crude product collected by filtration with a mixed solvent containing tetrahydrofuran (THF) and n-pentene,
    purifying a solution containing said extracted crude product by passing said solution through an alumina column, and
    recrystallizing the purified solution to obtain a purified product of a $Ru(Cp)_2$ complex;

wherein
the weight ratio of tetrahydrofuran to n-pentane in said mixed solvent (tetrahydrofuran/n-pentane) is from 5/5 to 2/8.

5. The method of claim 1, wherein said deposition inhibitor is selected from the group consisting of glass wool, silica gel, alumina, and activated carbon.

6. The method of claim 1, wherein the content of sodium or potassium, or both, in the sublimate after passage through the deposition inhibitor is 5 ppm or less.

7. The method of claim 1, further comprising forming a ruthenium-containing film from the sublimate after passage through the deposition inhibitor.

8. The method of claim 2, wherein the content of calcium in the recrystallized purified product is 5 ppm or less.

9. The method of claim 2, further comprising forming a ruthenium-containing film from the recrystallized purified product.

10. The method of claim 3, wherein said column is an alumina column.

11. The method of claim 3, wherein the content of iron or nickel, or both, in the purified product after passage through the column is 5 ppm or less.

12. The method of claim 3, further comprising forming a ruthenium-containing film from the purified product after passage through the column.

13. The method of claim 4, wherein the content of zinc in the purified product is 5 ppm or less.

14. The method of claim 4, further comprising forming a ruthenium-containing film from the purified product.

* * * * *